US005593879A

United States Patent [19]
Steller et al.

[11] Patent Number: 5,593,879
[45] Date of Patent: Jan. 14, 1997

[54] **CELL DEATH GENES OF *DROSOPHILA MELANOGASTER* AND VERTEBRATE ANALOGS**

[75] Inventors: Hermann Steller, Natick; John M. Abrams; Megan E. Grether, both of Cambridge; Kristin White, Lynnfield, all of Mass.

[73] Assignee: Massachusetts Institute of Technology, Cambridge, Mass.

[21] Appl. No.: 123,343

[22] Filed: Sep. 17, 1993

Related U.S. Application Data

[63] Continuation-in-part of Ser. No. 4,957, Jan. 15, 1993.

[51] Int. Cl.$^6$ .............................. C12N 1/00; C12N 5/10; C12N 15/12; C12N 15/63
[52] U.S. Cl. .................................... 435/240.1; 435/252.3; 435/254.11; 435/320.1; 536/23.5
[58] Field of Search ....................... 536/23.5; 435/320.1, 435/252.3, 240.1; 935/11, 66

[56] References Cited

PUBLICATIONS

Padgett et al. (1987) Nature 325: 81–84.
Bryant (1988) Developmental Biology 128: 386–395.
Ramos et al. (1993) Genes and Development 7: 2533–2547.
Horikawa et al. (1966) Nature 210: 183–185.
Hotz, Michel A. et al., "Changes in Nuclear Chromatin Related to Apoptosis or Necrosis Induced by the DNA Topoisomerase II Inhibitor Fostriecin in MOLT–4 and HL–60 Cells Are Revealed by Altered DNA Sensitivity to Denaturation," *Experimental Cell Research*, 201:184–191, (1992).
Gougeon, Marie–Lise et al., "Evidence for an Engagement Process Towards Apoptosis in Lymphocytes of HIV–infected Patients," *C.R. Acad. Sci. Paris*, t. 312, Série III:529–537, (1991). (Article in French with an Abridged English Version).

Bynum, S.V., "Morphogenesis of Retinoic Acid–Induced Postaxial Polydactyly in Mice," *Teratology*, 43:1–9, (1991).
Peiffer, Robert L., et al., "Relationship of Cell Death to Cyclophosphamide–Induced Ocular Malformations," *Teratogenesis, Carcinogenesis, and Mutagenesis*, 11:203–212, (1991).
Compton, Mark M., et al., "Analysis of Glucocorticoid Actions on Rat Thymocyte Deoxyribonucleic Acid by Fluorescence–Activated Flow Cytometry," *Endocrinology*, 122(5):2158–2164, (1988).
Holtz, M. A., et al., "Changes in nuclear chromatin related to apoptosis or necrosis induced by the DNA topoisomerase II inhibitor fostriecin in MOLT–4 and HL–60 cells are revealed by altered DNA sensitivity to denaturation", *Chemical Abstracts* 117:(11), Sep. 14, 1992, abstract no. 103690.

(List continued on next page.)

*Primary Examiner*—Robert A. Wax
*Assistant Examiner*—G. E. Bugaisky
*Attorney, Agent, or Firm*—Hamilton, Brook, Smith & Reynolds, P.C.

[57] ABSTRACT

The present invention relates to cell death genes, which are genes required for programmed cell deaths; mutant organisms, in which embryonic programmed cell death occurs to a less than normal extent; proteins encoded by the cell death genes; antibodies which bind the cell death gene products; and agents which alter the ability of cell death genes to cause programmed death of cells. As described herein, Applicants have identified two genes which function in the initiation of apoptosis or programmed cell death. These two genes, referred to respectively as the reaper (rpr) gene and the head involution defective (hid) gene, map to position 75C1,2 on the third chromosome in *Drosophila (D.) melanogaster* and, as described in detail below, exhibit expression patterns related to the pattern of cell death during Drosophila embryogenesis; mutations in each gene reduce levels of cell deaths or abolish cell death.

6 Claims, 9 Drawing Sheets

PUBLICATIONS

Gougeon, M. L., et al., "Evidence for an engagement process towards apoptosis in lymphocytes of HIV–infected patients", *Chemical Abstracts* 115(23), Dec. 9, 1991, abstract no. 253977.

Bynum, S. V., "Morphogenesis of retinoic acid–induced postaxial polydactyly in mice", *Chemical Abstracts* 114(21), May 27, 1991, abstract no. 199621.

Peiffer, R. L. et al., "Relationship of cell death to cyclophosphamide–induced ocular malformations", *Chemical Abstracts* 116(15), Apr. 13, 1992, abstract no. 143411.

Compton, M. M., et al., "analysis of glucocorticoid actions on rat thymocyte deoxyribonucleic acid by fluorescence–activated flow cytometry", *Chemical Abstracts* 108(25), Jun. 20, 1988, abstract no. 216521.

Abbott, M. K. and Lengyel, J. A., "Embryonic Head Involution and Rotation of Male Terminalia Require the Drosophila Locus head involution defective," *Genetics*, 129:783–789 (1991).

Fischbach, K. F. and Technau, G., "Cell Degeneration in the Developing Optic Lobes of the sine oculis and small–optic–lobes Mutants of *Drosophila melanogaster*," *Dev. Biology*, 104:219–239 (1984).

Kerr, J. F. R. and Harmon, B. V., "Definition and Incidence of Apoptosis: An Historical Perspective," In *Cell Death in Biology and Pathology* (eds. I. D. Bowen and R. A. Lockshin), Chapman and Hall, London, pp. 5–29 (1991).

Spreij, T. E., "Cell Death During the Development of the Imaginal Disks of *Calliphora Erythrocephala,*" *Netherlands J. Zool.*, 21(3):221–264 (1971).

Oppenheim, R. W., et al., "Naturally Occurring and Induced Neuronal Death in the Chick Embryo in Vivo Requires Protein and RNA Synthesis: Evidence for the Role of Cell Death Genes," *Dev. Biology*, 138:104–113 (1990).

Raff. M. C., "Social Controls on Cell Survial and Cell Death," Nature, 356:397–400 (1992).

Ellis, R. E., et al., "Mechanisms and Functions of Cell Death," *Annu. Rev. Cell. Biol.*, 7:663–698 (1991).

Saunders, Jr., J. W., "Death in Embryonic Systems," *Science*, 154:604–612 (1966).

Umansky, S. R., "Apoptotic Process in the Radiation–Induced Death of Lymphocytes," *In Apoptosis: the Molecular Basis of Cell Death* (eds. 1. d. Tomei and F. O. Cope), Cold Spring Harbor Laboratory Press, New York, pp. 193–208 (1991).

Wolff, T. and Ready, D. F., "Cell Death in Normal and Rough Eye Mutants of Drosophila," *Development*, 113:825–839 (1991).

Jackson, F. R., et al., "Product of per locus of Drosophilia shares homology with proteoglycans," *Nature* 320(13):185–188 (1993).

Abrams, J. M., et al., "Programmed cell death during Drosophila embryogenesis", Development 117:29–43 (1993).

Segraves, W. A., and Hogness D. S., "The E75 ecdysone–inducible gene responsible for the 75B early puff in *Drosophila* encodes two new members of the steroid receptor superfamily", *Genes & Development* 4:204–219 (1990).

MacKay, W. J., and Bewley, G. C., "The Genetics of Catalase in *Drosophila melanogaster*: Isolation and Characterization of Acatalasemic Mutants", *Genetics Society of America* 122:643–652 (1989).

```
1           10            30            50           60
            .             .             .            .
    AATCATTGAATAAGAGAGACACCAGAACAAAGTGAACGAACTCGAAAATACGAAAGCAAA 61          70            90            110          120
            .             .             .            .
    GTGTGTGCGCCAGTAACAAAGAACTAACTCGATAAATATTCATTGTGCAGAAGAGAAAGT 121         130           150           170          180
            .             .             .            .
    TATTGAGTCACTACCAGTTGTGTAATTCCGAACGAGAAGAAAGATAAACCAACAACAATG
                                                              Met 181         190           210           230          240
            .             .             .            .
    GCAGTGGCATTCTACATACCCGATCAGGCGACTCTGTTGCGGGAGGCGGAGCAGAAGGAG
                                           |||||||||||||||||||||
                                           CGGGAGGCGGAGCAGAAGGAG

AlaValAlaPheTyrIleProAspGlnAlaThrLeuLeuArgGluAlaGluGlnLysGlu 241         250           270           290          300
            .             .             .            .
    CAGCAGATTCTCCGCTTGCGGGAGTCACAGTGGAGATTCCTGGCCACCGTCGTCCTGGAA
    ||||||||  ||||||||||||||||||| |||||||||||||||||||||| ||||||||
    CAGCAGATCCTCCGCTTGCGGGAGTCCCAGTGGAGATTCCTGGCCACCGTTGTCCTGGAA
            C                   C                    T
    GlnGlnIleLeuArgLeuArgGluSerGlnTrpArgPheLeuAlaThrValValLeuGlu 301         310           330           350          360
            .             .             .            .
    ACCCTGCGCCAGTACACTTCATGTCATCCGAAGACCGGAAGAAAGTCCGGCAAATATCGC
    ||  |||||||
    ACGCTGCGCC
      G
    ThrLeuArgGlnTyrThrSerCysHisProLysThrGlyArgLysSerGlyLysTyrArg 361         370           390           410          420
            .             .             .            .
    AAGCCATCGCAATGAGGATTCGAGTAACTAACAAATACGGGGAAAACCAATAGTCCAGTC

LysProSerGlnEnd 421         430           450           470          480
            .             .             .            .
    CAAAATCCAGAGTACAAAGGAAATAAGCATGAGCCAACCCAAAACCCAAACACGTCACCA
```

FIG. 2A

```
481           490            510            530           540
         CTCATCAGCCGACGGCACTCGATTTCTACTGCAGTCAAGGACACAGAGCCACAACACCCA 541           550            570            590           600
         CCCAATTTTAGTTTACTCATCAAAGCGATTGTGATAATGGTTTTGTTTCTACAAAAAAGC 601           610            630            650           660
         GGAGGAAAAATTTGAAAAAAATAACGTTTTTATAAAGTCCCCAATTTTTTACAAAAATGT 661           670            690            710           720
         TTTAATGATATAAATCAACTTTTTTAGAAATAATTTACTCTTAAAGCCTATTTAAATGAA 721           730            750            770           780
         TTACTACTGTAATAGTTTGTAAGTTCTTTTTGTAAGACGAGTTTTTCTAAGTTTTTTTAA 781           790       798
         GAAGAAACCCCAGAAAAA
```

FIG. 2B

GENOMIC STRUCTURE OF HID

```
   1  tctgccgacgtcgcggtagaggctctgttgccgtagtttgaggccccagngcgaacagtt   60
  61  cattttagccgcggagccagtaagacgtgtttcctgccctctttctttgagtctgcgac  120
 121  acgttttaagtgctcttccataattgacaacagcaaaagcaaagaataaaaaaataACAA  180
 181  AAAATAAAAAACGAAATCCATCGTGAACAGTTTTGTGTTTTTAAATCAGTTCTAAACACG  240
 241  AAAAGGGTTGATGAAAAACGCAGAAGAATCCGAAAAACTAACTAACCGAGCAAAAACTTG  300
 301  ACTTGAGTGTTGTTTGACAAATCAGGAAAGATAAAAAACAAATCATAAGAAAAAACTGCA  360
 361  CGAAAAATGAAAAGTTTCTAATATTCAAAATCTTGCACAAGAAATACAAAATCAATTAA   420
 421  AGTGAACTCTAACCAAAAGTTGTACACAAAATAAAAAGCAAAACAAAGCAGCAAGAACA   480
 481  ATCACAAGAAGAGCAAAGTGCCAACAAAGTGCAGGAAGGAAGGAAGCGGATAAGGACAAA  540
 541  AAGGAAGCCAGCACACACACACACACACCCACACAATGGCCGTGCCCTTTTATTTGCCCG  600
                                        MetAlaValProPheTyrLeuProG 601  AGGGCGGCGCCGATGACGTAGCGTCGAGTTCATCGGGAGCCTCGGGCAACTCCTCCCCCC  660
      luGlyGlyAlaAspAspValAlaSerSerSerSerGlyAlaSerGlyAsnSerSerProH 661  ACAACCACCCACTTCCCTCGAGCGCATCCTCGTCCGTCTCCTCCTCGGGCGTGTCCTCGG  720
      isAsnHisProLeuProSerSerAlaSerSerSerValSerSerSerGlyValSerSerA 721  CCTCCGCCTCCTCGGCCTCATCTTCGTCCTCCGCATCGTCGGACGGCGCCAGCAGCGCCG  780
      laSerAlaSerSerAlaSerSerSerSerAlaSerSerAspGlyAlaSerSerAlaA 781  CCTCGCAATCGCCGAACACCACCACCTCGTCGGCCACGCAGACGCCGATGCAGTCTCCAC  840
      laSerGlnSerProAsnThrThrThrSerSerAlaThrGlnThrProMetGlnSerProL 841  TGCCCACCGACCAAGTGCTATACGCCCTCTACGAGTGGGTCAGGATGTACCAGAGCCAGC  900
      euProThrAspGlnValLeuTyrAlaLeuTyrGluTrpValArgMetTyrGlnSerGlnG 901  AGAGTGgtaagtctacaaagatctcaattctccactcttaagaactttgaaattgtgtgg  960
      lnSerA 961  gttaatcaggatatccatttagtttacctcaaatacatttgcagatacaaaaataagctt 1020
1021  ttcgattcatatacggttattaattgcgaaatgtttaacgtaagttcccacacagaataa 1080
1081  cgtc..........gtttgatttcttattatgtgccaactgtatttaaattgtcattcg  1140
1141  cttaactttcgtttcagCCCCGCAAATCTTCCAGTATCCGCCGCCAAGCCCCTCTTGCAA 1200
                       laProGlnIlePheGlnTyrProProProSerProSerCysAs 1201  TTTCACTGGCGGCGATGTGTTCTTTCCGCACGGCCATCCGAATCCGAACTCGAATCCCCA 1260
      nPheThrGlyGlyAspValPhePheProHisGlyHisProAsnProAsnSerAsnProHi 1261  TCCACGTACCCCCCGAACCAGCGTGAGCTTCTCCTCCGGCGAGGAGTACAACTTCTTCCG 1320
      sProArgThrProArgThrSerValSerPheSerSerGlyGluGluTyrAsnPhePheAr 1321  GCAGCAGCAGCCGCAACCACATCCGTCATATCCGGCGCCATCAACACCGCAGCCAATGCC 1380
      gGlnGlnGlnProGlnProHisProSerTyrProAlaProSerThrProGlnProMetPr 1381  ACCGCAGTCAGCGCCGCCGATGCACTGCAGCCACAGCTACCCGCAGCAGTCGGCGCACAT 1440
      oProGlnSerAlaProProMetHisCysSerHisSerTyrProGlnGlnSerAlaHisMe 1441  GATGCCACACCATTCCGCTCCCTTCGGAATGGGCGGTACCTACTACGCCGGCTACACGCC 1500
      tMetProHisHisSerAlaProPheGlyMetGlyGlyThrTyrTyrAlaGlyTyrThrPr 1501  GCCACCCACTCCGAACACGGCCAGTGCGGGCACCTCCAGCTCATCGGCGGCCTTCGGCTG 1560
      oProProThrProAsnThrAlaSerAlaGlyThrSerSerSerSerAlaAlaPheGlyTr 1561  GCACGGCCACCCCACAGCCCCTTCACGTCGACCTCCACGCCGTTATCGGCGCCAGTGGC 1620
      pHisGlyHisProHisSerProPheThrSerThrSerThrProLeuSerAlaProValAl 1621  GCCCAAGATGCGCCTGCAGCGCAGCCAGTCGGATGCGGCCAGACGgtgagtagccagcga 1680
      aProLysMetArgLeuGlnArgSerGlnSerAspAlaAlaArgAr 1681  tgcagggtgccaaaagatacactgcctgggtggtgcaaatcaaatcaaactgtaatttag 1740
1741  attcagatcgatgagcatacagaataagagggaaagttccgaactatgacatgataggat 1800
1801  gccatttagaccaagtaaaatatacaaagctatacacagattgtat..........gcta 1860
```

FIG. 3A

| | | |
|---|---|---|
| 1861 | cacaaacccgaatcgaatccgaaccgactgataattgctcatgacgttccaagtcaaccg | 1920 |
| 1921 | tctatatgtgcagcgatatttatagtcccnttatgcgtctcttcccacagCAAGCGATTG | 1980 |
| |                                                 gLysArgLeu | |
| 1981 | ACCTCGACGGGCGAGGATGAGCGCGAGTACCAGAGCGATCATGAGGCCACTTGGGACGAG | 2040 |
| | ThrSerThrGlyGluAspGluArgGluTyrGlnSerAspHisGluAlaThrTrpAspGlu | |
| 2041 | TTTGGCGATCGCTACGACAACTTTACGGCCGGCCGGGAGCGTCTGCAGGAGTTCAATGGA | 2100 |
| | PheGlyAspArgTyrAspAsnPheThrAlaGlyArgGluArgLeuGlnGluPheAsnGly | |
| 2101 | CGCATCCCGCCCCGGAAGAAGAAGAGCTCCAATAGCCACTCGAGCAGCAGCAATAATCCA | 2160 |
| | ArgIleProProArgLysLysLysSerSerAsnSerHisSerSerSerSerAsnAsnPro | |
| 2161 | GTCTGCCATACCGACAGCCAGTCCGGTGGTACATCCCAAGCGGAGAGCGGTGCCATCCAT | 2220 |
| | ValCysHisThrAspSerGlnSerGlyGlyThrSerGlnAlaGluSerGlyAlaIleHis | |
| 2221 | GGCCACATCAGTCAGCAGCGACAGGTGGAGCGAGAACGACAAAAGGCGAAGGCCGAGAAG | 2280 |
| | GlyHisIleSerGlnGlnArgGlnValGluArgGluArgGlnLysAlaLysAlaGluLys | |
| 2281 | AAGgtaagaaatggccaccaatcttggaatgcacaacgcatacagagaaagggtattctc | 2340 |
| | Lys | |
| 2341 | gtttcggttaatcagtatc..........aaagcaacttgttctttatgtttaagatttg | 2400 |
| 2401 | ccttcacgtgcacctgaatataactaaatgctatttttctattctcctttcagAAACCA | 2460 |
| |                                                       LysPro | |
| 2461 | CAGAGCTTCACTTGGCCAACTGTTGTGACCGTTTTCGTTTTGGCCATGGGCTGTGGCTTC | 2520 |
| | GlnSerPheThrTrpProThrValValThrValPheValLeuAlaMetGlyCysGlyPhe | |
| 2521 | TTTGCGGCGCGATGAAAGCGCAGGAGACGTGTAATCGAATGATCTATAGTGAAATCAGCT | 2580 |
| | PheAlaAlaArgEnd | |
| 2581 | AGCCCTTAAGATACATCCGATCTAAACTTAGTTGTAGTTAAACCGTACATAANTGCAACG | 2640 |
| 2641 | AATTTATTGAACTGCAGGAGC   2661 | |

FIG. 3B

SEQUENCE OF HID CDNA 5A1B

```
   1 TGACAAAAAATAAAAAACGAAATCCATCGTGAACAGTTTTGTGTTTTTAAATCAGTTCTA   60
  61 AACACGAAAAGGGTTGATGAAAAACGCAGAAGAATCCGAAAAACTAACTAACCGAGCAAA  120
 121 AACTTGACTTGAGTGTTTGTTTGACAAATCAGGAAAGATAAAAAACAAATCATAAGAAAAA  180
 181 ACTGCACGAAAAATGAAAAAGTTTCTAATATTCAAAATCTTGCACAAGAAATACAAAATC  240
 241 AATTAAAGTGAACTCTAACCAAAAGTTGTACACAAAATAAAAAGCAAAACAAAGCAGCGA  300
 301 AGAACAATCACAAGAAGAGCAAAGTGCCAACAAAGTGCAGGAAGGAAGGAAGCGGATAAG  360
 361 GACAAAAAGGAAGCCAGCACACACACACACACCCACACAATGGCCGTGCCCTTTTATTTG  420
   1                                                MetAlaValProPheTyrLeu    7

421 CCCGAGGGCGGCGCCGATGACGTAGCGTCGAGTTCATCGGGAGCCTCGGGCAACTCCTCC  480
   8 ProGluGlyGlyAlaAspAspValAlaSerSerSerGlyAlaSerGlyAsnSerSer      27

481 CCCCACAACCACCCACTTCCCTCGAGCGCATCCTCGTCCGTCTCCTCCTCGGGCGTGTCC  540
  28 ProHisAsnHisProLeuProSerSerAlaSerSerSerValSerSerSerGlyValSer   47

541 TCGGCCTCCGCCTCCTCGGCCTCATCTTCGTCATCCGCATCGTCGGACGGCGCCAGCAGC  600
  48 SerAlaSerAlaSerSerAlaSerSerSerSerAlaSerSerAspGlyAlaSerSer      67

601 GCCGCCTCGCAATCGCCGAACACCACCACCTCGTCGGCCACGCAGACGCCGATGCAGTCT  660
  68 AlaAlaSerGlnSerProAsnThrThrThrSerSerAlaThrGlnThrProMetGlnSer   87
                                            1(3)05014:     ↓
 661 CCACTGCCCACCGACCAAGTGCTATACGCCCTCTACGAGTGGGTCAGGATGTACCAGAGC  720
  88 ProLeuProThrAspGlnValLeuTyrAlaLeuTyrGluTrpValArgMetTyrGlnSer  107
                                 ▼
 721 CAGCAGAGTGCCCCGCAAATCTTCCAGTATCCGCCGCCAAGCCCCTCTTGCAATTTCACT  780
 108 GlnGlnSerAlaProGlnIlePheGlnTyrProProProSerProSerCysAsnPheThr  127

781 GGCGGCGATGTGTTCTTTCCGCACGGCCATCCGAATCCGAACTCGAATCCCCATCCGCGC  840
 128 GlyGlyAspValPhePheProHisGlyHisProAsnProAsnSerAsnProHisProArg  147

841 ACCCCCCGAACCAGCGTGAGCTTCTCCTCCGGCGAGGAGTACAACTTCTTCCGGCAGCAG  900
 148 ThrProArgThrSerValSerPheSerSerGlyGluGluTyrAsnPhePheArgGlnGln  167
             A22:    T
 901 CAGCCGCAACCACATCCGTCATATCCGGCGCCATCAACACCGCAGCCAATGCCACCGCAG  960
 168 GlnProGlnProHisProSerTyrProAlaProSerThrProGlnProMetProProGln  187

961 TCAGCGCCGCCGATGCACTGCAGCCACAGCTACCCGCAGCAGTCGGCGCACATGATGCCA 1020
 188 SerAlaProProMetHisCysSerHisSerTyrProGlnGlnSerAlaHisMetMetPro  207

1021 CACCATTCCGCTCCCTTCGGAATGGGCGGTACCTACTACGCCGGCTACACGCCACCACCC 1080
 208 HisHisSerAlaProPheGlyMetGlyGlyThrTyrTyrAlaGlyTyrThrProProPro  227

1081 ACTCCGAACACGGCCAGTGCGGGCACCTCCAGCTCATCGGCGGCCTTCGGCTGGCACGGC 1140
 228 ThrProAsnThrAlaSerAlaGlyThrSerSerSerAlaAlaPheGlyTrpHisGly     247
                                            A206:   T
1141 CACCCCCACAGCCCCTTCACGTCGACCTCCACGCCGTTATCGGCGCCAGTGGCGCCCAAG 1200
 248 HisProHisSerProPheThrSerThrSerThrProLeuSerAlaProValAlaProLys  267
         A206:    T                              ▼
1201 ATGCGCCTGCAGCGCAGCCAGTCGGATGCGGCCAGACGCAAGCGATTGACCTCGACGGGC 1260
 268 MetArgLeuGlnArgSerGlnSerAspAlaAlaArgArgLysArgLeuThrSerThrGly  287
                A329:    A
1261 GAGGATGAGCGCGAGTACCAGAGCGATCATGAGGCCACTTGGGACGAGTTTGGCGATCGC 1320
 288 GluAspGluArgGluTyrGlnSerAspHisGluAlaThrTrpAspGluPheGlyAspArg  307

1321 TACGACAACTTTACGGCCGGCCGGGAGCGTCTGCAGGAGTTCAATGGACGCATCCCGCCC 1380
 308 TyrAspAsnPheThrAlaGlyArgGluArgLeuGlnGluPheAsnGlyArgIleProPro  327
                                                         W:  C
1381 CGGAAGAAGAAGAGCTCCAATAGCCACTCGAGCAGCAGCAATAATCCAGTCTGCCATACC 1440
 328 ArgLysLysLysSerSerAsnSerHisSerSerSerSerAsnAsnProValCysHisThr  347
```

FIG. 4A

```
                  W:    C
1441  GACAGCCAGTCCGGTGGTACATCCCAAGCGGAGAGCGGTGCCATCCATGGCCACATCAGT  1500
 348  AspSerGlnSerGlyGlyThrSerGlnAlaGluSerGlyAlaIleHisGlyHisIleSer   367
                                                             ▼
1501  CAGCAGCGACAGGTGGAGCGAGAACGACAAAAGGCGAAGGCCGAGAAGAAGAAACCACAG  1560
 368  GlnGlnArgGlnValGluArgGluArgGlnLysAlaLysAlaGluLysLysLysProGln   387

1561  AGCTTCACTTGGCCAACTGTTGTGACCGTTTTCGTTTTGGCCATGGGCTGTGGCTTCTTT  1620
 388  SerPheThrTrpProThrValValThrValPheValLeuAlaMetGlyCysGlyPhePhe   407

1621  GCGGCGCGATGAAAGCGCAGGAGACGTGTAATCGAATGATCTATAGTGAAATCAGCTAGC  1680
 408  AlaAlaArgEnd                                                   410

1681  CCTTAAGATATATGCCGATCTAAACATAGTTGTAGTTAAACCGTACATAAGTGCAACGAA  1740
1741  TTTATTGAACTGCAGGAGCGAAAGCAGAAAGTCATTAATTCGTAAACGGATTGTTAGATA  1800
1801  CACAAACAGCCAACATACACGAAGAGTGTGCCTAAGATTAAGAAGGTTGACGGGACACAA  1860
1861  GAACAATATATTCTATCTGTCTATGGTAACTGCATTTGTATTTCTAAAACGAAACGAAAG  1920
1921  ATAACAATCTTAACTGCTCAAAGTAATGAAAACTCTTAGACTGGCAAGAGACTCAAATCA  1980
1981  CACTTATTTTTTGCTGATCCATATTTTTGTACAACCTTTGAGCGATATTTACAAATTA    2040
2041  TACTAGTACAAAAAAAGAGAGAGAGAGATAAGCAAAAGAAAACTGCCACTTTTGAGATA   2100
2101  CTTTTGATAATCTTTGATTTGCATTTAATCATTTCCACACTTGCATTTTTATAAACAAC   2160
2161  AAACAAAATTACTTCCATTGTAGAACAAAGTAAACTGCAATTTCAATGTCTTCGCATTTG  2220
2221  TAATTCCGAATTGCAAGAAAAACAAAAATATTTAAATATGTTTAACTAGTAGAATTTTT   2280
2281  TAAACGTAAGTCCACAAAAACAAGCACATCTAGCTTTAATTGTTGAAACAAAAGCAGAAA  2340
2341  AAACGCAACAAAAAAATGAATGAAAATCATTAAATTAATTTTGTATATAGTTTTTATGCC  2400
2401  ATTTTTGTGATGTTTTGTGTCTACGGTTTATGTCATGTTATTTTAGTTAAATTTCTTATG  2460
2461  ATTTATGTTTATTTGTAATATTTTTTGTCATTGTTTGTTCATCATCATATTCAAATTGGT  2520
2521  CTCACAATATAATAGTTTTAAGCTCCACGCCCGGGAGATTGATGGCAAAACGATTGAAAT  2580
2581  TTGGCCAGAAGAGAGATAGTTTTCCCCATTCGTACACAGTCTTTTTTGGAATGCACATTA  2640
2641  ATGATCTCTCACAATGGAAATTAATGAAAATTGATCTCCGCAGCTAGCCAAAGTTAAAAA  2700
2701  AGAAATGAAGAGGAAAACATATTCTATAGGCAATTTTCACTATATGCTAGAATTTCCCGG  2760
2761  GCGTTTCAATGCTAATCGAATACAGTGACATGAAAGCAAACATAGCGAAATATTAAGAA   2820
2821  AATCAATCAAAAGAAAGAAAAACCAATTCCCAAAAATCGCATTGATCTCATGGATTTAT   2880
2881  ACAATACAATTACATCAACCGTTTTTTTACAATGAGAAATGTTATAAAAAGCAGAAAGTG  2940
2941  AAACACAGAAACATAAACAAAAATTAACGAAAAGCTTAGATATAAGTTCGCCAAGCGTTT  3000
3001  TAGTTCTATTTTCTAGAATGTCTAAGTCGGTTTAGTGAGTTTATTAAGCTGTCTTCGGAC  3060
3061  ACAAGTTTATTTGTATATAAGCAATATTATTTGTGTAGCCTAAGTGACAGTCCCAATCAA  3120
3121  ATCCAATCCAATATCACCCAGTCCCGGACATTTCCCAGCAAAACAATAGACTATTCTCGC  3180
3181  GTTCACATGTATCAATCTTAATTTGAATTACCACAAAATGAAATGAAATACTAAAACCAT  3240
3241  ACACAAATGAAAATTATTTTTGTAAATTGTTTGCATCAAGTGAGCAAGGGATTAGATT    3300
3301  AAGGAATCATCCTTGCTTTATCCCCTGCTTATTGCTAATTAGTTTTCACAATGATCTCGG  3360
3361  TAAAGTTTTGTGGCCTTGCGCCCAAAAGTCGTACAGATTTTGGTTTGCCATAAATACTC   3420
3421  GAACAAAAAGTTAATGAAAAACGAAGCAAATGGAAAAAAAATCAGAATGAAACACAAGAA  3480
3481  ATTTATATTTTTGACCCAATGCTACTTAATCCGTTTTTGTAATTTAAGTATCTTTACTCG  3540
3541  ACCTTGTATATAGCGCAGTTCGAATCACAGAATCAAATGCCATTTTTGTATAGAATTTTA  3600
3601  TTTGGTGCCAAAACAGTGACAGATAATTAAATGTCTATGAACCCGTGTATTTCGCATATT  3660
3661  ATACATTTATACATATATCGTAACTTCAATGATAAGTTTGATTCTGAAATTTTGTCAACT  3720
3721  CAATTTAAGAAACATTTCTGTTGTAGTTTAGTGATTGCTAGCAGAAAGCACTTTGTTTAA  3780
3781  TTGTACATTTTATATTATGCTGTAATATTTTAATATACATAAATATCATTATTGATCTCA  3840
3841  TGAATATGTTCATAAGACAACAAAAATTATATATATGAATACATCTATGTGTATGTGTAA  3900
3901  AG    3902
```

FIG. 4B

MOLECULARLY CHARACTERIZED *hid* ALLELES

Allele:

1) l(3)05014   P-element insertion at nucleotide 714, between amino acids 105 and 106

2) 40C        imprecise exision of l(3)05014   leaves 38 extra bases at a. a. 103

3) 8D         imprecise exision of l(3)05014   leaves 40 extra bases at a. a. 103

```
Canton-s  698  GAGTGGGTCAGGATGTAC                                                            CAGAGCCAGC
40C       698  GAGTGGGTCAGGATGTACCATGATGAAATAACAT  T  TTATTTCATCATGGATGTGGATGTACCAGAGCCAGC
8D        698  GAGTGGGTCAGGATGTACCATGATGAAATAACATA    TGTTATTTCATCATGGATGTGGATGTACCAGAGCCAGC
                                target                 5'P              3'P      target
                               duplication                                      duplication
```

4) A22     amino acid 170    CCA to TCA    Pro to Ser

5) A206    amino acid 261    TCG to TTG    Ser to Leu

6) A206    amino acid 274    CAG to TAG    Gln to End

7) A329    amino acid 301    TGG to TGA    Trp to End

8) W       amino acid 346    CAT to CCT    His to Pro

9) W       amino acid 451    TCC to CCC    Ser to Pro

10) ML66   splice donor mutation - junction between exons 2 and 3

Canton-S   AG/gt .... tcag/AA
ML66       Ag/at .... tcag/AA

FIG. 5

CELL DEATH GENES OF *DROSOPHILA MELANOGASTER* AND VERTEBRATE ANALOGS

FUNDING

This work is supported in whole or in part by the Howard Hughes Medical Institute, Pew Scholars Award, the American Cancer Society and the National Institutes of Health. The United States Government has certain rights in the invention.

RELATED APPLICATION

This application is a continuation in-part of U.S. Ser. No. 08/004,957, entitled "Assays for Cell Death and Uses Therefor", filed Jan. 15, 1993. The teachings of U.S. Ser. No. 08/004,957 are incorporated herein by reference.

BACKGROUND

The elimination of cells via programmed cell death is a prominent feature of normal development throughout the animal kingdom (Wyllie et al., *Nature* 284:555–557 (1980); Bowen and Lockshin, *Cell Death in Biology and Pathology*, Chapman and Hall (1981); Truman and Schwartz, *J. Neurosci.* 4:274 (1984); Ellis et al., *Annu. Rev. Cell Biol.* 7:663–698 (1991); Tomei and Cope, *Apoptosis: The Molecular Basis of Cell Death*, Cold Spring Harbor Laboratory Press, New York, (1991); Yuan and Horvitz, *Dev. Biol.* 138:33–41 (1990); Raff, *Nature* 356:397–400 (1992)). In many organisms, a large number of cells die in the absence of obvious external insults. For example, vertebrate neurogenesis produces about twice as many neurons as are needed in the mature nervous system, and approximately half of these neurons are eliminated by cell death (Cowan et al., *Science* 225:1258 (1984)). This "natural" death process occurs in a morphologically characteristic and reproducible way, referred to as apoptosis (Kerr et al., *Br. J. Cancer* 26:239–257 (1972); Kerr et al., *Perspectives on Mammalian Cell Death* (ed C. S. Potten), Oxford University Press, England, p. 93 (1987); Kerr and Harmon, *Apoptosis: The Molecular Basis of Cell Death* (eds. Tomei, L. D., and Cope, F. O.), Cold Spring Harbor Laboratory Press, New York, pp. 5–29 (1991); Lockshin and Zakeri, *Apoptosis: The Molecular Basis of Cell Death* (eds. Tomei, L. D., and Cope, F. O.), Cold Spring Harbor Laboratory Press, New York, p. 47–60 (1991)). During apoptotic death, the cytoplasm and nucleus of the dying cell condense, while the morphology of cellular organelles remains rather well preserved. In many cases, the cell breaks up into fragments (apoptotic bodies) and is eventually engulfed by phagocytic cells. In contrast, externally induced cellular injury (e.g., as the result of temperature shocks, lack of oxygen, some toxic chemicals) results in necrosis (reviewed by Kerr and Harmon, *Apoptosis: The Molecular Basis of Cell Death* (eds. Tomei, L. D., and Cope, F. O.), Cold Spring Harbor Laboratory Press, New York, pp. 5–29 (1991)). Necrotic deaths are characterized by a general swelling of the cell and its organelles, loss of membrane integrity, lysosomal rupture and cellular disintegration.

It is now generally supposed that apoptosis is the result of an active cellular program, comparable to cell differentiation. In some cases, this developmental program of cell death appears to be triggered by systemic hormones, trophic factors, and local cell interactions (Truman, *Ann. Rev. Neurosci.* 7:171–188 (1984); Oppenheim, *Trends Neurosci.* 8:487–493 (1985); Campos, A. R. et al., Development 114:355–366 (1992)). In many instances, apoptotic deaths have been found to depend on RNA and protein synthesis within the dying cell (Martin et al., *J. Cell Biol.* 106:829–844 (1988); Oppenheim et al., *Dev. Biol.* 138:104–113 (1990); Fahrbach and Truman, *Soc. Neurosci. Abst.* 14:368 (1988); Kimura and Truman, *J. Neurosci.* 10:403–411 (1990); Scott and Davies, *J. Neurobiol.* 21:630 (1990)), suggesting that the activity of genes is required for controlling and/or executing programmed cell death. However, despite its importance in animal development, little is known about the genetic and molecular mechanisms underlying programmed cell death.

SUMMARY OF THE INVENTION

The present invention relates to cell death genes, which are genes required for programmed cell deaths; mutant organisms, in which embryonic programmed cell death occurs to a less than normal extent; proteins encoded by the cell death genes; antibodies which bind the cell death gene products; and agents which alter the ability of cell death genes to cause programmed death of cells. As described herein, Applicants have identified two genes: reaper (rpr), which is required for apoptosis or programmed cell death and the head involution defective (hid) gene which is a strong candidate for an apoptosis gene. Both genes map to position 75C1,2 on the third chromosome in *Drosophila (D.) melanogaster*; they exhibit sequence similarities in their N-terminal sequences. As described in detail below, both genes exhibit expression patterns related to the pattern of cell death during Drosophila embryogenesis; deletions of these genes abolish cell death and mutations in hid have been shown to reduce cell death.

Applicants have identified a small genomic deletion which blocks virtually all programmed cell deaths that normally occur during Drosophila embryogenesis, providing evidence that the mutation deletes a central control function for the induction of programmed cell death (apoptosis) and identified a gene, designated reaper (rpr), which has a central control function for the initiation of cell death in *Drosophila melanogaster*. Reintroduction of a 25 Kb DNA into a cell death deficient mutant restores cell death to a significant extent. Onset of expression of the rpr gene precedes the first morphological signs of apoptosis and its pattern of expression is strikingly similar to the pattern of cell death during Drosophila embryogenesis. The rpr gene is expressed in dying cells. The reaper gene is approximately 1.3 kb and maps to a 100 kb interval within the cell death defective deletion Df(3L)H99 which, as described herein, must contain at least part of a function required for the initiation of apoptosis. This is the first example known to Applicants of a gene expressed predictably prior to appearance of the first morphological signs of apoptosis and specifically, in the cells analyzed, in cells destined to die. In addition, Applicants have shown that X-ray irradiation rapidly induces widespread ectopic rpr expression; X-ray irradiation of Drosophila embryos had previously been shown to lead to massive ectopic apoptosis. (Abrams, J. et al., *Development* 117:29–43 (1992). Together, these two findings indicate that different ways of activating apoptosis induce rpr expression. Applicants have also shown that deletions in the rpr region provide considerable protection against X-ray induced cell death, further supporting the conclusion that multiple pathways for initiation of apoptosis converge onto the rpr gene and that the rpr gene encodes a central control function for cell killing. Further, Applicants have isolated rpr from three Drosophila species, *D. melanogaster, D. simulans* and *D. virilis*, which are approximately 60 million years apart in evolution. (Beverly, S. M. and A. C. Wilson, *M. Mol. Evol.* 21:1–13 (1984).

Applicants have also identified a second gene, the head involution defective (hid) gene, which maps to position 75C1,2 on the third chromosome, is contained within the Df(3L)H99 interval and exhibits a pattern of expression which overlaps with the pattern of programmed cell death. It gives rise to a mRNA transcript of approximately 4.5 kb. Mutations in the hid gene reduce the number of cell deaths in certain tissues, such as the wing disc and dorsal vessel (the primordia for the larval heart) and increase the number of certain cells, such as the larval photoreceptor neurons and the cardioblasts (cells which make up the larval heart). A mammalian homologue of hid has been identified in two different cell lines; hid has been shown to cross-hybridize with a single transcript of ~2 kb in both mammalian cell lines. Significantly, a signal was detected in HiB5 cells only in cells induced to undergo apoptosis. In PC12 cells, which are immortalized cells, constitutive expression was observed.

As a result of the work described herein, DNA required for the initiation of programmed cell deaths is available, as are RNA transcripts and the respective encoded gene products. Also available are probes, which can be all or a portion of the rpr or the hid gene or their corresponding RNA transcripts. These probes have been shown to be useful for identifying similar apoptosis genes in other cell types, including vertebrate cells, such as mammalian cells and especially human cells. DNA which hybridizes to rpr DNA, DNA which hybridizes to hid DNA and the product encoded by each are also the subject of this invention.

Also available is a method of identifying cells which are destined to die, before there is any morphological manifestation of programmed cell death. In one embodiment of this method, the occurrence (presence, absence or reduced quantity) of the presence of rpr RNA or DNA is assessed in cells. For example, the presence of rpr RNA can be assessed to identify cells destined to die. Alternatively, the absence of rpr DNA or RNA can be assessed as an indicator of the inability or reduced likelihood cells will die (e.g., to assess whether cells are immortalized or tumor cells, since it is reasonable to expect that tumor cells delete rpr or contain a non-functional or defective rpr gene). The pattern of expression of rpr RNA has been shown, in Drosophila, to be strikingly similar to the pattern of programmed cell death; this transcript is typically expressed in cells which will later die and, thus, is useful as a marker for identifying cells before it is otherwise evident they will die. As a result, the occurrence of cell death can be predicted and, if desired, its occurrence can be altered (i.e., enhanced or diminished, totally or partially, as to its timing and/or the extent to which it occurs). In a further embodiment, hid RNA or DNA is assessed.

A further aspect of the present invention is mutant organisms, particularly mutant Drosophila, such as *D. melanogaster*, in which programmed cell death occurs to a lesser extent, (including an absence of cell death) than occurs in wild type Drosophila, due to an alteration in a cell death gene which renders it less active or inactive or to deletion of the cell death gene. In particular, mutant Drosophila in which rpr gene function, hid gene function or rpr gene function and hid gene function are altered, with the result apoptosis is decreased, are the subject of this invention.

BRIEF DESCRIPTION OF THE DRAWINGS

FIGS. 2A and 2B show the partial nucleic acid sequence of reaper cDNA (rpr) (SEQ ID NO. 1) from *D. melanogaster* and the encoded amino acid sequence (SEQ ID NO. 2), as well as the DNA sequence of a segment of the rpr gene isolated from *D. simulans* (SEQ ID NO. 3).

FIGS. 3 (3A and 3B) is the genomic structure (DNA sequence, SEQ ID NO. 4, SEQ ID NO: 14, SEQ ID NO: 15 and SEQ ID NO: 16) of the hid gene and the deduced amino acid sequence of the encoded HID protein (SEQ ID NO. 5). Genomic DNA sequence is represented by lower case letters and cDNA sequence is represented by upper case letters. The gaps in the genomic sequence result from unsequenced intron portions; however, the CDNA sequence is complete.

FIG. 4 (4A and 4B) is the sequence of hid cDNA (SEQ ID NO. 6) and deduced amino acid sequence of the encoded HID protein (SEQ ID NO. 7).

FIG. 5 shows the DNA sequence of 8 different mutant alleles of hid (Canton-S, SEQ ID NO. 8; 40C, SEQ ID NO. 9; 8D, SEQ ID NO. 10).

DETAILED DESCRIPTION OF THE INVENTION

Figure 1:
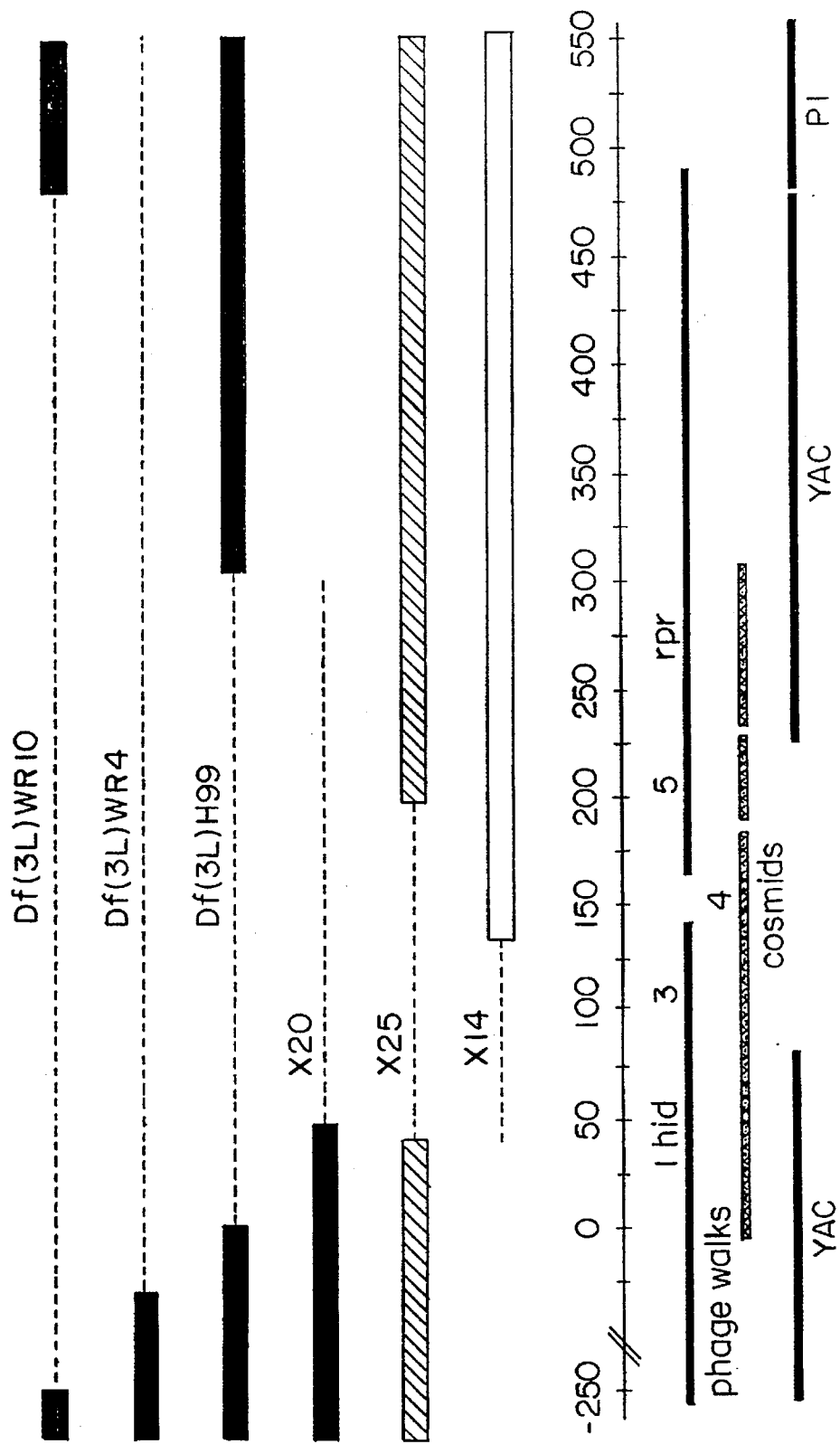
FIG. 1 is a graphic representation of 75C1,2 on which the deletion breakpoints for Df(3L)WR10, Df(3L)WR4, Df(3L)H99 X20, X25 and X14 and the locations of the hid gene and the rpr gene are indicated. The dotted lines indicate the deleted DNA segments.
Figure 6A:
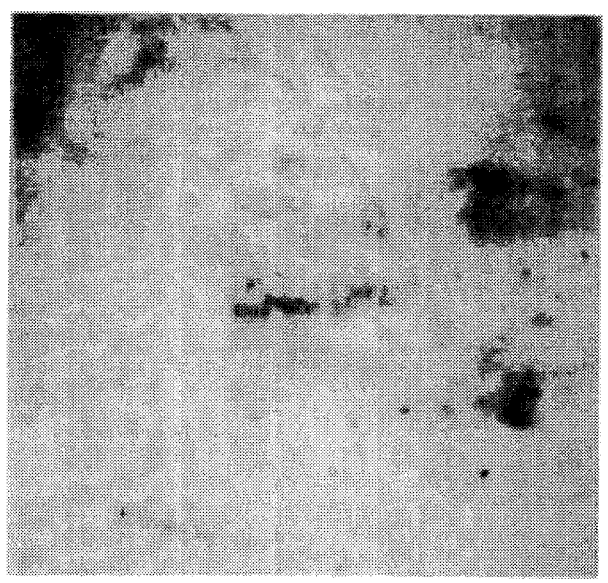
FIGS. 6A and 6B are photographs of results of Northern blots, using hid cDNA as a probe, which show specific cross hybridization with mammalian RNA in cell lines PC12 and HiB5.
Figure 6B:
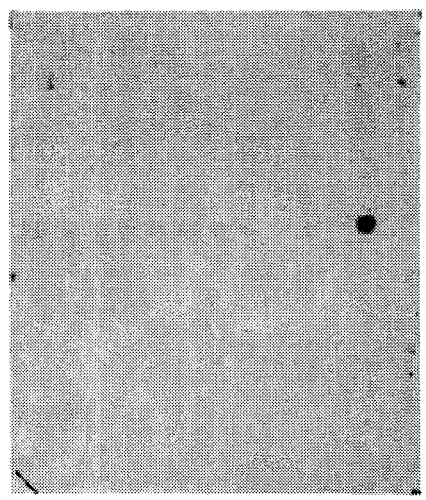

This invention relates to genes required for programmed cell death, referred to as cell death genes, and to their encoded RNA and protein products. Specifically, two cell death genes from *Drosophila melanogaster*, rpr and hid, have been cloned and characterized. These two genes are located in a 300 kb region, referred to as the Df(3L)H99 region, which maps to position 75C1,2 on the third chromosome. Deletion of the region abolishes virtually all programmed cell deaths that occur during normal Drosophila embryogenesis. A number of transcripts have been mapped to the Df(3L)H99 region (see FIG. 1). cDNA (SEQ ID NO. 1) encoding the 1.3 kb rpr mRNA and cDNA (SEQ ID NO. 4, SEQ ID NO: 14, SEQ ID NO: 15 and SEQ ID NO: 16 ) encoding the 4.5 kb hid mRNA have been cloned and sequenced (FIGS. 2 and 3). Amino acid sequences have been deduced from the cDNA sequences (SEQ ID NO. 2 and 5, respectively).

The rpr gene

Applicants have isolated the entire rpr gene through a chromosomal walk and has also obtained rpr cDNA. As described in Example 14, a cell death defective deletion Df(3L)H99 has been produced in *D. melanogaster*. Using other deletions, this 100 kb interval within the deletion has been shown to contain at least part of a function required for initiation of apoptosis in Drosophila. As also described (FIG. 1), the rpr gene maps to this 100 kb interval within Df(3L)H99 and has been assessed as to its role in apoptosis. Embryos homozygous for deletion X25 (FIG. 1) have only slightly reduced levels of cell death, compared to wild type Drosophila. Df(3L)H99 and the transheterozygote combination of Df(3L)H99 and deletion X20 are completely cell death defective. Deletion X14 has normal levels of cell death. See FIG. 1. A cosmid transgene isolated by Applicants and shown to contain the rpr transcription unit has been shown to restore significant levels of apoptosis in the cell death defective deletion, further supporting the role of the rpr gene in apoptosis (Example 16).

Expression of the rpr gene has been assessed and shown not only to occur in a pattern which is strikingly similar to the pattern which occurs during Drosophila embryogenesis, but to precede the first morphological signs of apoptosis (e.g., by approximately 1–2 hours in Drosophila). As described in Example 17, widespread ectopic rpr expression is rapidly induced by X-ray irradiation. X-ray irradiation of Drosophila embryos had previously been shown to lead to massive ectopic apoptosis. Abrams, J. et al., *Development* 117:29–43 (1992). Work described herein makes it reasonable to conclude that the ectopic apoptosis observed is due to expression of the rpr gene. In addition, the work described herein provides evidence that there are multiple mechanisms by which apoptosis is induced and that these converge on or have their effect through the rpr gene or its product. That is, multiple factors, including cell-cell interactions, x-ray irradiation and lineage, can turn on rpr, thus initiating cell death and, as further described herein, deletions in the rpr gene region offer considerable protection against cell death, such as cell death induced by x-ray irradiation. It is reasonable to conclude that this protection results from the unavailability of the rpr gene, which, therefore, cannot be expressed or otherwise carry out its central control function in cell killing.

As described in Example 14, the 1.3 kb rpr transcript maps to the region of the chromosomal walk indicated in FIG. 1 (i.e., approximately 275 kb from the left or distal breakpoint and approximately 25 kb from the right or proximal breakpoint of Df(3L)H99). Two independent cDNA clones for rpr have been isolated and sequenced. Their sequence is represented in FIG. 2 (SEQ ID NO. 1); the sequence of FIG. 2 is not full length (approximately 800 bp vs. approximately 1300 bp) but they contain relevant protein coding information. That is, translation from the first methionine (position 178 in FIG. 2) results in a peptide of 65 amino acids, as also shown in FIG. 2. Analysis of homologous DNA sequences in another Drosophila species, *D. simulans*, provides strong support that this open reading frame (ORF) is biologically relevant. A segment of the rpr gene was isolated, using PCR and primers described herein, from *D. simulans* and its DNA sequence was determined (SEQ ID NO. 3; FIG. 2). The primers used included:

HS#1, which is a 5' PCR oligo of the following sequence:

ATG-GCN-GTG-GCN-TTC-TA[C/T]-AT    (SEQ ID NO. 11)

Met-Ala-Val-Ala-Phe-Tyr-----Leu    (SEQ ID NO. 12)

(20 mer, Tm=56°–62° C., c=32) and

HS#3, which is a 3' PCR oligo of the following sequence:

CC -GGT-CTT-NGG-[A/G]TG-[A/G]CA    (SEQ ID NO. 13)

inverse of Cys-His-Pro-Lys-Thr-Gly (17 mer, Tm=52°–58° C., c=16)

Comparison of the *D. melanogaster* and *D. simulans* sequences showed four single nucleotide changes which are all silent changes in the third codon position (i.e., the changes do not alter the amino acid composition of the conceptual translation product). Since the probability of a random occurrence of all four changes in the third codon is low (1:81), Applicants conclude that selection operates to maintain the amino acid composition of the ORF. Thus, it is very likely that the predicted 65 amino acid peptide is a biologically relevant rpr gene product.

The hid gene

The 75C region contains a second gene, contained within Df(3L)H99, designated head involution defective or hid which results described herein support as a second cell death gene. That hid is a cell death gene is evidenced by the fact that it is contained within the Df(3L)H99 interval; its pattern of expression overlaps with the pattern of programmed cell death; and mutations in hid reduce the number of cell deaths in certain tissues and can increase the number of specific cell types. This is further supported by the fact that expression of an apparent mammalian hid homologue is induced when mammalian neuroepithelial stem cells are induced to undergo apoptosis.

Genomic and cDNA clones for hid which are essentially full length have been cloned and sequenced, using known methods, specifically sequencing of subclones in BlueScript, using the chain termination method and sequencing of double stranded templates, using the circumvent (Taq polymerase) procedure. The hid DNA sequence (SEQ ID NO. 4, SEQ ID NO: 14, SEQ ID NO: 15 and SEQ ID NO: 16) and predicted HID amino acid sequence (SEQ ID NO. 5) are shown in FIG. 3. The sequence of hid cDNA (SEQ ID NO. 6) and predicted HID amino acid sequence (SEQ ID NO. 7) are shown in FIG. 4. Sequence analysis of different hid alleles (FIG. 5) has established that this cDNA encodes hid function. For example, the lethal hid allele 1(3)05014 is caused by the insertion of a P-element transposon at position 707. In addition, revertants have been generated by precise excision of this P-element, demonstrating that the insertion is responsible for the mutant phenotype. A variety of chemically induced mutations and mutations which include a stop codon have also been sequenced (FIG. 5).

Strong evidence of mammalian homologues of hid has been obtained. Using the Drosophila cDNA fragment as a probe, specific cross hybridization with mammalian DNA and mRNA has been demonstrated. On Southern blots of DNA/DNA hybridization, a unique band was detected. DNA/RNA hybridization showed that RNA was detected in rat cell lines. Stringency condition used included 30% FAM (formamide), 42° C., 0.1 SDS, 5 ×SSC and 5 ×BFP (Denhardt's Solution). Results showed that hid cross hybridized with a single transcript of approximately 2 kb in two different mammalian cell lines, PC12 cells, which are rat adrenal pheo chromosytsoma cells, (Greene, L. A. and A. S. Tischler, *Proc. Natl. Acad. Sci.*, USA 73:2424–2428 (1976)) and in the neuroepithelial stem cell line HiB5 (Renfranz, P. J. et al., *Cell* 66:713–729 (1991)). A signal was detected only in HiD5 cells induced to undergo apoptosis.

As described herein and in co-pending application U.S. Ser. No. 08/004,957, entitled "Assays for Cell Death and Uses Therefor", filed Jan. 15, 1993, analysis of the hid and rpr genes has shown their involvement in programmed cell death. The pattern of cell death in Drosophila embryos homozygous for chromosomal deletions was examined to identify genes required for programmed cell death. (See Example 14). Three overlapping deletions (Df(3L)WR4, Df(3L)WR10 and Df(3L)Cat D104) resulted in embryos which lacked virtually all acridine orange (AO) staining at all stages of development, indicating that essentially no cell death deaths occurred in the embryos. These deletions overlap in genomic region 75C1,2 on the third chromosome. Applicants have shown that another, later-obtained mutation in this region, hid$^{H99}$ [(Abbott, M. K. and Lengyel, J. A., *Genetics* 129:783 (1991)], shows the same phenotype. It appears cytologically normal but molecular analysis revealed that hid$^{H99}$ is a deletion which is internal to the overlap of the previously described deficiencies (see FIG. 1).

Assessment of hid$^{H99}$ embryos was carried out to demonstrate that the lack of AO staining in hid$^{H99}$ embryos actually reflects a failure of cell death. For example, tissue sections were analyzed by light and transmission electron microscopy. No evidence of programmed cell death could be detected by either of these methods. Semithin sections were stained with sections were stained with toluidine blue/methylene blue/borax (Ashburner, *Drosophila. A Laboratory Manual* (Cold Spring Harbor Press, New York, (1989)). On examination by light microscopy, mutant embryos had no darkly stained cells, which are characteristic of apoptotic cell death. Electron microscopy (EM) confirmed the lack of cell death in mutant embryos. In the cylpeolabrum of a wild-type embryo, EM showed the electron dense cells typical of apoptotic cell death, which at this stage had mostly been engulfed by macrophages. All EM sections of wild-type embryos at this stage show many apoptotic cells. This is in stark contrast to homozygous $hid^{H99}$ embryos in which no features of apoptosis were detected at any stage of embryogenesis. These results supported the conclusion that programmed cell death does not occur in these mutant embryos.

In addition, the possibility that the lack of cell death in $hid^{H99}$ embryos results from a general block in development caused by the absence of functionally unrelated genes was addressed. Several observations led to the conclusion that this is extremely unlikely. First, mutants embryos reach advanced developmental stages. They form a segmented cuticle and begin to move, but fail to hatch. In addition, mutant embryos express markers which are only present in differentiated cells. Furthermore, mitotic clones of $hid^{H99}$ in the eye contained fully differentiated and morphologically normal photoreceptors neurons. This demonstrates that the $hid^{H99}$ deletion does not have general adverse effects on cell division, differentiation, or survival. Second, from a survey of more than 129 deletions (50% of the genome), only those in chromosomal region 75C1,2 resulted in the complete lack of all programmed cell deaths. Many of these other deletions had more adverse effects on embryogenesis, yet none was capable of completely blocking programmed cell death. Finally, as shown below, some apoptosis could be induced in $hid^{1H99}$ embryos upon X-ray irradiation. These results argue very strongly against a general, unspecific cellular defect, for example in energy metabolism or protein synthesis, as the underlying cause for the observed phenotype.

The absence of cell death in mutant embryos is expected to result in the presence of extra cells. This prediction was tested by counting specific cells in the central nervous system, a tissue which is subject to substantial amounts of cell death during wild-type development (Abrams et al., *Development* 117:29–44 (1993)). (Example 19) One cell type that normally undergoes programmed death in insects is the abdominal neuroblasts (Bate, *J. Embryol. Exp. Morph.* 35:107–123 (1976)). In Drosophila, approximately 25 cells are born in each abdominal neuromere, but only 6 cells persist to eventually produce neurons in the imaginal ganglia (Campos-Ortega and Hartenstein, *The Embryonic Development of Drosophila melanogaster* (Springer Verlag, New York, (1985); Truman and Bate, *Dev. Biol.* 125–145 (1988); Prokop and Technau, *Development* 111:79 (1991)). Use of the elf-1 antibody to visualize these cells (Bray et al., *Genes & Development* 3:1130–1145 (1989)) showed that their number was dramatically increased in mutant embryos. While approximately six cells stain in each abdominal neuromere in the wild-type nervous system, there were 20 or more cells staining in some of the abdominal segments of the mutant nervous system. This result demonstrates the presence of supernumerary neuroblasts in fully developed $hid^{H99}$ embryos, confirming the expectation that a block of cell death should lead to an increase in the number of these cells.

An antibody towards the Kruppel protein was used to label a subset of cells in the late embryonic central nervous system (Gaul et al., *Cell* 50:639–647 (1987)). In mutant embryos, the overall size of the central nervous system was significantly increased. Cell counts revealed that this antibody stained 2 to 3 fold more cells in the ventral nerve cord of mutant embryos of identical age. Finally, there also appeared to be a similar increase in the number of cells in the larval photoreceptor organ. These experiments demonstrate the presence of many extra cells in the nervous system of mutant embryos. Interestingly, the magnitude of cell death in the Drosophila nervous system, as estimated by these markers approximates that seen in C. elegans and vertebrates (Ellis and Horvitz, *Cell* 44:817–829 (1986)). Insertion of a transposable P element in the coding region of the hid gene (see FIG. 1) reduces the number of programmed cell deaths that normally occur during development. Excision of the transposon results in reversion of the cell death-defective phenotype. Transgenic rescue experiments, in which the cell death phenotype in deletion mutants lacking the Df(3L)H99 region is rescued by a transgene containing the hid gene, also indicate the cell death activity of this gene. (Example 16)

The Df(3L)H99 deletion mutant exhibits a severely defective mutant phenotype, in which virtually no programmed cell deaths occur. A smaller deletion, Df(3L)X25 (FIG. 1), exhibits a reduced number, but not complete abolishment, of programmed cell deaths. Heterozygous Df(3L)H99/Df(3L)X25 mutants, obtained by crossing the two deletion mutants, have a more dramatic reduction of apoptosis, exhibiting about 10% of the cell death which occur in wild type phenotype, exhibiting about half the number of cell deaths that occur in the Df(3L)X25 mutant. These results suggest that a gene present in two copies in the X25 homozygous mutant, in one copy in the heterozygous mutant, and absent in the H99 mutant contributes to activation of programmed cell deaths. The rpr transcript maps to this interval (FIG. 1). Transgenic rescue experiments have shown that the rpr gene is able to partially rescue cell death-defective deletion mutants.

As also described herein, nucleic acid hybridization analysis of genomic DNAs from several vertebrate species, including human and mouse, show that sequences similar to the Drosophila hid are present in these species. Applicants' studies show that programmed cell deaths occurring during Drosophila embryogenesis have morphological characteristics identical to the apoptosis observed in the development of other, including vertebrate, animals (see below), suggesting that similar mechanisms of programmed cell death exist in various species. Thus, it is reasonable to expect that analogs of the cell death genes hid and rpr function in vertebrate and other species.

Induction of cell death could be induced in $hid^{H99}$ embryos upon X-ray irradiation was examined. (Example 19) Ionizing radiation induces apoptosis in mammalian cells (Potten et al., *Cell. Tissue Kinet.* 11:149 (1978); Umansky, *Apoptosis: The Molecular Basis of Cell Death*, (eds. Tomei, L. D. and Cope, F. O.) (Cold Spring Harbor Press, New York (1991); Lowe et al., *Nature* 362:847 (1993); Clarke et al., *Nature* 362:849 (1993)) and Drosophila wild-type embryos (Abrams et al., *Development* 117:29–44 (1993)), but appears to involve different control mechanisms than developmentally regulated programmed cell death (Lowe et al., *Nature* 362:847 (1993); Clarke et al., *Nature* 362:849 (1993)). When $hid^{H99}$ embryos were irradiated, some AO staining was induced. However, in mutants the induction of ectopic cell death was much less efficient than in wild-type, requiring higher doses of radiation, and resulting in many fewer staining cells. Therefore, this mutation provides a significant degree (approximately 100-fold) of protection against radiation induced cell death. In those cells in which death does occur, analysis showed that the cells are morphologically indistinguishable from the apoptotic deaths seen during normal development. Cells in the mutant embryo are thus capable of undergoing apoptosis, even though they do not do so during normal development. Furthermore, apoptotic cells in mutant embryos become targets for engulfment by macrophages. We conclude that the defect in the hid$^{H99}$ embryos lies upstream of the terminal cellular events of apoptosis. Once induced, the basic cell death program can apparently be executed in mutant embryos and, as in wild-type embryos, apoptotic corpses can be recognized and phagocytosed by macrophages. Taken together, the results indicate that hid$^{H99}$ deletes a function of central importance for the initiation of programmed cell death in Drosophila.

A large number of developmental mutants in Drosophila lead to ectopic cell death (Abrams et al., *Development* 117:29 (1993); Fristrom, *Molec. Gen. Genetics* 103:363 (1969); Murphy, *Devel. Biol.* 39:23 (1974); Fischbach and Technau, *Dev. Biol.* 104:219 (1984); Martinez-Arias, *J. Embryol. Exp. Morphol.* 87:99 (1985); Steller et al., *Cell* 50:1139 (1987); Klingensmith et al., *Devel. Biol.* 134:130 (1989); Bonini et al., *Cell* 72:379 (1993); Tepass and Knust, *Roux's Arch. Dev. Biol.* 199:189 (1990); Magrassi and Lawrence, *Development* 113:825 (1991)). We were interested in determining whether the cell death function in the hid$^{H99}$ interval was required for such ectopic deaths. The crumbs mutation leads to widespread defects in the development of the epithelial tissues, followed by massive cell death during embryogenesis (Tepass and Knust, *Roux's Arch. Dev. Biol.* 199:189 (1990)). In the double mutant crumbs hid$^{H99}$ virtually no AO staining was observed, demonstrating that hid$^{H99}$ is capable of blocking the massive ectopic death normally seen in crumbs mutant (data not shown). These data indicate that hid$^{H99}$ can be used as a general tool for blocking cell death. Therefore, it should now be possible to critically assess the role of cell death in the context of both normal and mutant development.

The function deleted by hid$^{H99}$ could either affect a universal extracellular signalling pathway that selects which cells will die, or the initiation of the cell death program itself. The former possibility can be excluded, because it would require a single ubiquitous cell death signal. During Drosophila embryogenesis, a large number of cells die in a variety of different places and developmental stages. The onset of some of these cell deaths appears to involve cell-cell interactions, while others may be determined by lineage (Abrams et al., *Development* 117:29 (1993); Bate *J. Embryol. Exp. Morph.* 35107 (1976); Magrassi and Lawrence, *Development* 104:447 (1988); Bate et al., *J. Neurosci.* 1:103 (1981)). Given the great variety of circumstances under which cell death can occur, it is difficult to imagine that all these deaths could be induced by a common signal. Furthermore, x-ray induced cell death almost certainly involve a different pathway. Indeed, a number of mutations have been identified in Drosophila which affect cell death in particular tissues (Fischbach and Technau, *Dev. Biol.* 104:219 (1984); Steller and Rubin, *Cell* 50:1139 (1987); Cagan and Ready, *Genes Dev.* 3:109 (1989); Kimura and Truman, *J. Neurosci.* 10:403 (1990); Wolff and Ready, *Development* 113:825 (1991); Campos et al., *Development* 114:355 (1992); Fristrom, *Molec. Gen. Genetics* 103:363 (1969); Murphy, *Devel. Biol.* 39:23 (1974); Fischbach and Technau, *Dev. Biol.* 104:219 (1984); Martinez-Arias, *J. Embryol. Exp. Morphol.* 87:99 (1985); Steller et al., *Cell* 50:1139 (1987); Klingensmith et al., *Devel. Biol.* 134:130 (1989); Bonini et al., *Cell* 72:379 (1993); Tepass and Knust, *Roux's Arch. Dev. Biol.* 199:189 (1990); Magrassi and Lawrence, *Development* 113:825 (1991)). These mutations are likely to influence cell death by affecting such a tissue specific signalling event, or by more generally altering the cellular environment. In contrast, the hid$^{H99}$ mutant appears to globally block the initiation of apoptosis. In this regard, it is similar to the ced-3 and ced-4 mutations which prevent the onset of all programmed cell deaths in the nematode *C. elegans* (Ellis and Horvitz, *Cell* 44:817 (1986)).

Results presented herein demonstrate that programmed cell death in Drosophila is under genetic control. Despite the considerable morphological and developmental diversity of cell deaths seen in this organism, these results support the initiation of all these deaths through a common pathway. The ability to selectively block programmed cell deaths in Drosophila by mutations, such as hid$^{H99}$, provides a powerful tool for studying the role of cell death during wild-type and mutant development. The molecular characterization of rpr and related genes will provide important insight into the biochemical basis of programmed cell death in Drosophila, and possibly other organisms as well (30).

Utility of the Invention

As a result of the work described herein, nucleotide sequences of two Drosophila cell death genes, hid and rpr, and their encoded amino acid sequences are provided. DNAs, RNAs, oligonucleotides, polypeptides and peptides derived from all or portions of these sequences are thus available; they can be chemically synthesized or recombinantly produced using methods known in the art (see, e.g. Ausubel et al. (eds.), *Current Protocols in Molecular Biology*, Greene Publishing Associates and Wiley-Interscience, New York, 1989). Antibodies, both polyclonal and monoclonal, can be raised against the HID and RPR polypeptides, or antigenic portions of these polypeptides, using known immunization or recombinant methods (see, e.g. Harlow and Lane, *Antibodies: A Laboratory Manual*, Cold Spring Harbor Laboratory, 1988; Moore, *Clin. Chem.* 35(9):1849–1853 (1989)).

The above molecules are useful as probes in a variety of methods for detecting nucleic acids and proteins. These methods include nucleic acid hybridization, polymerase chain reaction (PCR) amplification of DNA or RNA, immunological assays and Western blot analysis, and computerized sequence comparisons with databases. Using these probes and methods, analogs of the hid gene and analogs of the rpr gene from other species can be identified and cloned. hid gene analogs, rpr gene analogs and their encoded products from other vertebrates, particularly mammals and specifically humans, are the subject of this invention. An analog of rpr DNA or hid DNA (a rpr gene analog or hid gene analog) is DNA which functions in cell death in a manner similar to that described herein for the rpr gene and the hid gene, respectively. An analog of the encoded rpr gene product or of the encoded hid gene product is encoded by the respective gene analog or hid gene analog. DNA and RNA which hybridize to hid DNA, hid RNA, rpr DNA or rpr RNA under standard hybridization conditions and in cell death (i.e., are cell death genes or gene transcripts) are also the subject of the present invention. As described above, Applicants have demonstrated that humans and rats have genomic sequences similar to the Drosophila cell death genes. The probes are also useful for studying the expression of the cell death genes: the amount of expression, the tissue specificity of expression, the developmental pattern of expression, and the effect of other genes, mutations, hormones and other regulatory factors and environmental conditions on expression. The correlations between abnormal expression of these genes, at the RNA or protein levels, and certain pathologies can be examined and may lead to diagnostic tests for these diseases.

Furthermore, expression vectors suitable for expressing these cell death genes in a host cell can be constructed. A variety of expression vector/host cell systems, both prokaryotic and eukaryotic, are known in the art. Cell lines and transgenic animals that express the hid and rpr genes can also be generated.

Mutated genes and RNA and polypeptide products with reduced or enhanced cell death activity are described herein, and others can be produced by known mutagenesis techniques (e.g. Ausubel, 1989 supra). Mutant cell lines, mutant Drosophila and mutant transgenic animals can also be generated. The rpr gene or hid gene or an encoded product can also be used for cell ablation, since such genes are killer or cell death genes. Introducing rpr DNA, hid DNA and/or an encoded product into a cell, in which the gene is expressed, or the encoded product is functional can result in cell death. For example, tumor cells, in which rpr or hid might be deleted or nonfunctional, can be killed, for example, by introducing rpr, hid or their respective encoded product.

Nucleic acids, proteins, and peptides bearing the cell death sequences of hid, rpr, or their vertebrate analogs may be useful as drugs for enhancing or reducing cell deaths. Drugs that decrease or increase programmed cell deaths are expected to be useful for treating pathologies involving excessive cell deaths, e.g. degenerative diseases, stroke, trauma and injury, viral and other infections, or abnormally low occurrence of cell deaths, e.g. cancer, respectively. Previous studies suggest that abnormal activation of programmed cell death may be a feature of degenerative, especially neurodegenerative, diseases, and that defective cell death may contribute to the development of certain cancers (Horvitz and Chalfie, In Neurodegenerative Disorders: Mechanisms and Prospects for Therapy (eds. Price et al.) (1991); Bargman, Current Biology 1:388 (1991); Hockenbery et al., Nature 348:334–336 (1990); Williams, 1991)). Furthermore, drugs that inhibit cell death may be useful for preserving organs and grafts for transplants, and drugs that increase cell death may be useful for killing or controlling the proliferation of undesirable animals, such as pests and parasites, disease-bearing or agriculturally damaging insects, and recombinant animals. Active cell death proteins, or portions of these proteins, may also be used as toxins to kill cells, such as cancerous cells, lymphocytes involved in autoimmune recognition, cells infected with a virus, or parasites in the body.

The molecules can be delivered by known methods, such as gene therapy, or using pharmaceutical carriers. Characterization of the functional domains of these molecules should provide a basis for drug design, and analogs of the active domains can be developed. For example, active peptide portions of the cell death proteins can be conjugated to cell type-specific antibodies to provide toxins that are targeted for certain cell populations. On the other hand, antisense oligonucleotides derived from cell death gene sequences can be used to inhibit cell death.

It may be found that cell death genes of other species can complement the function of the Drosophila genes and vice versa. This can be determined by introducing foreign cell death genes as transgenes into cell death-defective Drosophila mutants. Drosophila cell death genes can also be put under the control of tissue specific or inducible promoter and expressed in transgenic animals, such as mice. Alternatively, expression vectors containing Drosophila cell death genes can also be introduced, by transfection or other known methods, into cultured cells to see if cell death is induced. Cells that are subjected to toxic conditions can be used to assay the inhibitory effects of antisense oligonucleotides derived from cell death genes.

The following sections describe in further detail the staining assay that was used to screen for cell death-defective mutants, the screening of multigene deletion mutations, characterization of the $hid^{H99}$ mutation, molecular analysis of the Df(3L)H99 interval region, cloning and characterization of the hid and rpr genes, transgenic rescue and in situ hybridization experiments, and identification of vertebrate analogs of hid.

Cell Death Assay

Applicants were able to screen for cell death- defective mutants in an efficient manner using an assay that they developed. As described in Examples 3–5, they found that the vital dyes acridine orange (AO), a fluorescent dye, and Nile blue (NB) can be used to visualize programmed cell deaths in live Drosophila embryos. The dyes have a selective affinity for dying cells and are able to penetrate the tissues of the embryo. Indeed, the dyes were found to stain apoptotic cell corpses inside engulfing phagocytes, without staining the phagocytes themselves. The assay requires preliminary removal of the embryonic chorion with bleach, followed by permeabilization of the waxy coat with heptane or octane. The stained cells are then visualized by conventional microscopy and Nomarski optics, in the case of NB, or fluorescent microscopy, in the case of AO. Tissue sections can also be prepared from the stained embryos to obtain higher resolution of the cell structures.

AO was found to selectively stain apoptotic cells, whereas NB stains both apoptotic and necrotic cells. Since the vast majority of programmed cell deaths are apoptotic, both vital dyes were found to be useful for visualizing programmed cell deaths.

Using this assay, Applicants were able to determine the extent and pattern of programmed cell deaths occurring throughout Drosophila embryogenesis, including those affecting the development of certain organs and body systems (Example 7).

Screen for Cell Death Defective Mutants

In Drosophila, as in vertebrates, cell death is regulated to a large extent by epigenetic factors such as hormonal cues (Kimura and Truman, J. Neurosci. 10:403–411 (1990)) or cell interactions (Fischbach and Technau, Dev. Biol. 104:219–239 (1984); Wolff and Ready, Development 113:825–839 (1991); Campos et al., Development 114:355–366 (1992)). Although mutations in some Drosophila genes have been reported to influence the pattern of cell death, no cell death defective mutations per se have yet been isolated in this organism.

Applicants have sought to identify such mutations without making any assumptions about their viability. Their approach has been to examine the pattern of cell death in embryos homozygous for previously characterized chromosomal deletions. Since more that 50% of the Drosophila genome is represented by such deletions, they were able to rapidly screen a substantial fraction of the genome for the existence of genes required to undergo programmed cell death. Although these deletions typically include genes essential for viability, the large maternal supply of household functions (Garcia-Bellido et al., J. Mol. Gen. Genet. 192:253–263 (1983)) permits development well beyond the stage at which cell death begins. Embryos homozygous for these deletions typically reach advanced stages of embryogenesis, but fail to hatch as larvae.

This method of obtaining cell death-defective mutants is based on the following rationale. First, given the large scale of programmed cell deaths that occur during embryonic development, cell death-defective mutants in Drosophila may be unable to successfully complete embryogenesis. Consequently, such a mutant may not be detected in genetic screens that assume adult viability. Second, this approach does not exclude somewhat pleiotropic genes, i.e. genes that are important for apoptosis but also contribute to other vital aspects of development, which would not easily be identified in screens for adult mutants. Finally, this approach permits rapid screening of more than half of the Drosophila genome and uses large multigene deletion mutants that are already available.

In wild type, a substantial amount of apoptotic cell deaths occur during embryogenesis in a relatively predictable pattern. Using the vital dye AO or NB, as described above, these dying cells can be followed in live embryos for extended periods. From the analysis of 129 multigene deletions (approximately 50% genome coverage), three deletions Df(3L)WR4, Df(3L)WR10 (Segraves and Hogness, *Genes & Development* 4:204–219 (1990)), and Df(3L) Cat$^{DH104}$ (Mackay and Bewley, *Genetics* 122:643–652 (1989)) were found that lacked virtually all AO staining in homozygous embryos at all stages of development. These deletions overlap in a genomic region at position 75C1,2 on the third chromosome. The overlapping interval is referred to as the Df(3L)H99 region. Another mutation in this region, hid$^{H99}$ (Abbott and Lengyel, Genetics 129:783–789 (1991)) was also identified that shows a similar phenotype. Molecular analysis revealed that hid$^{H99}$ is a small deletion in the Df(3L)H99 interval. A chromosomal walk from starting points O and 550 of FIG. 1 was carried out, using known methods. (Segraves, W. A. and D. S. Hogness, *Genes & Dev.* 4:204–219 (1990); Bender, W. et al., *J. Supramolec. Struc. (suppl.)* 3:32 (1979); Bender, W. et al., *J. Mol. Biol.* 168:17–33 (1983).

Characterization of the hid$^{H99}$ Mutant

To demonstrate that the lack of AO staining in hid$^{H99}$ embryos actually reflects a defect in programmed cell death, tissue sections were analyzed by light and transmission electron microscopy. No evidence of programmed cell death could be detected by either of these methods. All EM sections of wild type embryos showed many apoptotic cells. In contrast, homozygous hid$^{H99}$ embryos were completely devoid of apoptotic cells at any stage of embryogenesis. Because hid$^{H99}$ embryos reach advanced stages of development (see below), the possibility can be excluded, that the observed cell death defect results from an early developmental arrest.

Whether the absence of cell death in mutant embryos would result in the presence of extra cells was determined by counting specific cells in the central nervous system, a tissue which is subject to substantial amounts of cell death during wild type development (Abrams et al., *Development* 117:29–44 (1993)). One cell type that normally undergoes programmed death in insects is the abdominal neuroblast (Bate, *J. Embryol. Exp. Morph.* 35:107–123 (1976)). Approximately 25 neuroblasts are born in each abdominal neuromere (Campos-Ortega and Hartenstein, *Development* 114:355–366 (1985)), but only 6 of these cells persist to eventually produce neurons in the imaginal ganglia (Truman and Bate, *Dev. Biol.* 125:145–157 (1988); Prokop and Technau, *Development* 111:79–88 (1991)). Using the elf-1 antibody (Bray et al., *Genes & Development* 3:1130–1145 (1989)), which stains neuroblasts, to visualize these cells, it was found that the number of persistent cells dramatically increased in mutant hid embryos. An antibody (Kr) towards the Krüppel protein, which labels a subset of cells in the late embryonic central nervous system (Gaul et al., *Cell* 50:639–647 (1987)), as well as the nuclei of the larval photoreceptor organ, was also used. Again, this antibody was found to stain 2- to 3-fold more cells in the ventral nerve cord of mutant embryos than in wild type embryos of identical age. In addition, the overall size of the central nervous system was significantly increased in mutant embryos.

Next, Applicants examined whether cell death could be induced in hid$^{H99}$ embryos upon X-ray irradiation. X-rays induce apoptosis in mammalian cells (Umansky et al., *Apoptosis: The Molecular Basis of Cell Death* (eds. Tomei, L. D. and Cope, F. O.,) (Cold Spring Harbor Press, New York (1991)) and Drosophila wild type embryos (Abrams et al., *Development* 117:29–44 (1993)). When hid$^{H99}$ embryos were irradiated, some AO staining was induced. These embryos contained electron dense, pycnotic cells indistinguishable from those seen in wild type embryos. Macrophages that had engulfed dead cells were also observed, indicating that engulfment of cell corpses can still occur. Cells in mutant embryos are thus capable of undergoing apoptosis, even though they fail to do so during normal development. Considerable protection against x-ray irradiation-induced cell death was observed. These results argue strongly against a general, nonspecific cellular defect, for example, in energy metabolism or protein synthesis, as the underlying cause for the observed phenotype. Rather, they suggest that the induction of programmed cell death is blocked by the hid$^{H99}$ deletion.

Taken together, these results indicate that hid$^{H99}$ deletes a function of central importance for the induction of programmed cell death in Drosophila. It is possible, that this cell death function is encoded by more than one gene, since saturation mutagenesis for lethal and visible mutations produced only a single complementation group, head involution defective (hid) (Abbott and Lengyel, *Genetics* 129:783–789 (1991)) in the hid$^{H99}$ interval. None of the 16 previously isolated hid alleles showed any significant effect on AO staining; six of these hid alleles were isolated by Applicants and ten by Abbott and co-workers. Although it is possible that cell death-defective mutations produce morphologically normal flies, this is unlikely, because of the widespread nature of cell death during Drosophila development (Wolff and Ready, *Development* 113:825–839 (1991); Abrams et al., *Development* 117:29–44 (1993); Campos-Ortega and Hartenstein, *The Embryonic Development of Drosophila melanogaster* (Springer Verlag, New York) (1985)). It is more likely that the inability to identify cell death-defective single gene mutations is due to the presence of redundant functions in the hid$^{H99}$ interval, and that only deletions removing several of these genes will show a detectable phenotype. There are several examples in Drosophila of genomic regions containing two or more functionally redundant genes (Côté et al., *EMBO J.* 6:2793–2801 (1987); Grossniklaus et al., *Genes Dev.* 6:1030–1051 (1992); Schrons et al., *Genetics* 132:481–503 (1992)).

The lack of cell death in hid$^{H99}$ embryos is also unlikely to result from general developmental abnormalities caused by the absence of several functionally unrelated genes. From a survey of more than 50% of the genome, only deletions in chromosomal region 75C1,2 resulted in the lack of virtually all programmed cell deaths. In addition, mutant embryos are normal in many respects. They develop a segmented cuticle and begin to move, but fail to hatch. Furthermore, mitotic clones of hid$^{H99}$ in the eye were found to contain fully differentiated and morphologically normal photoreceptor neurons. This demonstrates that the hid$^{H99}$ deletion does not have general adverse effects on cell division, differentiation, or survival. Because it is possible to induce apoptosis in hid$^{H99}$ embryos with X-rays, it can further be concluded that the hid$^{H99}$ interval contains gene(s) required for the induction of a cell death program.

Molecular Analysis of the Df(3L)H99 Region

FIG. 1 shows the results of molecular analysis of the genomic region containing the DF(3L)H99 interval. About 700 kb of genomic DNA was cloned by "phage walking" in both directions from the position labelled zero. The cosmid library described in Example 17 and standard methods were used for the phage walking. (*Current Protocols in Molecular Biology*, ed. F. M. Ausubel et al., John Wiley & Sons, New York, 1993; J. Sambrook et al., *Molecular Cloning: A Laboratory Manual*, 2d ed., Cold Spring Harbor Laboratory Press, Cold Spring Harbor, N.Y., 1989) Sequence analysis of cDNAs made from this region indicates eight transcribed regions. Of these, hid and rpr fall in the Df(3L)H99 deletion interval. Cosmids were obtained that contain these transcribed regions.

The present invention is illustrated by the following Examples, which are not intended to be limiting in any way.

EXAMPLE 1

Cell Death in the Drosophila Embryo Occurs by Apoptosis

Comparative studies from a wide variety of organisms have defined a set of strikingly conserved morphological features associated with the regulated death of cells during development (Kerr et al., *Br. J. Cancer* 26:239–257 (1972); Wyllie et al., *Nature* 284:555–557 (1980)). This type of death, conventionally referred to as apoptosis or programmed cell death, involves a generalized condensation of the cytoplasm and nucleus, separation of the dying cell from its neighbors, fragmentation into discrete membrane-bound bodies and eventual engulfment of cellular debris and corpses by phagocytes (Kerr et al., *Br. J. Cancer* 26:239–257 (1972); Wyllie et al., *Nature* 284:555–557 (1980)). A characteristic of apoptotic death is that, in spite of these cytologic changes, organelles (e.g. mitochondria) remain intact and are often identifiable even after engulfment (Kerr and Harmon, In *Apoptosis: The Molecular Basis of Cell Death* (eds. Tomei, L. D., and Cope, F. O.) (Cold Spring Harbor Laboratory Press, New York, pp. 5–29) (1991)). In contrast, a distinctly different set of ultrastructural features are typically observed under conditions that induce cellular injury or necrosis (Wyllie, *In Cell Death in Biology and Pathology* (eds. Bowen, I. D. and Lockshin, R. A.), (Chapman and Hall, London, pp. 9–34) (1981); Kerr and Harmon, In *Apoptosis: The Molecular Basis of Cell Death* (eds. Tomei, L. D., and Cope, F. O.) (Cold Spring Harbor Laboratory Press, New York, pp. 5–29) (1991)). This form of death includes a general swelling of the cell and its organelles, loss of membrane integrity, lysosomal rupture and ultimate disintegration of organelles (for example, see Trump et al., *Cell Death in Biology and Pathology* (eds. Bowen, I. D., and Lockshin, R. A.), (Chapman and Hall, London, pp. 9–34) (1981); Wyllie, *Cell Death in Biology and Pathology* (eds. Bowen, I. D., and Lockshin, R. A.) (Chapman and Hall, London, pp. 9–34) (1981)).

Applicants have examined the ultrastructural morphology of embryonic cell death in Drosophila in order to determine if it resembles the apoptotic cell deaths previously observed in other systems. Electron microscopic images of a stage 13 embryo at various stages of cellular degeneration were compiled. At this point during embryogenesis, cell death is prominent and widespread. The resemblance of these degenerating bodies to the apoptotic figures that have been described in other animal systems is striking. Early signs of programmed cell death, i.e. compaction of chromatin into dark masses adjacent to the nuclear membrane and loss of cellular volume, are seen in the micrographs. The mitochondria are clearly identifiable and apparently unaffected. As degeneration progresses, dying cells separate from their neighbors, becoming further condensed and osmiophilic. At this stage, fragmentation into membrane-bound bodies often ensues. While nuclear components become highly compacted, the condensing cytoplasm frequently contains intact mitochondria. Dying cells and corpses can exist as free, unengulfed material, or more often, they are observed inside large phagocytes that may contain several degenerate bodies. From these analyses, it appears that the engulfment of cell corpses during embryogenesis occurs mostly, if not exclusively, by circulating macrophage-like cells (see below).

The stage at which a dying cell becomes a target for engulfment is apparently quite variable. Late stage apoptotic bodies, which are deteriorated to the extent that organelles are no longer identifiable, are frequently seen to be in phagocytic contact with macrophages. Some dying cells that have been completely phagocytosed, however, contain identifiable mitochondria and other organelles characteristic of earlier stages of degeneration. Macrophages have also been observed approaching cells showing only very early signs of death. For example, a cell in a very early stage of apoptosis (its nucleus only partially osmiophilic) is seen to be in close contact with an engulfing macrophage. Thus, while many dying cells are engulfed at a fairly late stage of degeneration when the entire cell is fully condensed, there are also instances of early engulfment prior to complete compaction of the nucleus. From these ultrastructural analyses, it is clear that the vast majority of natural cell deaths in the Drosophila embryo occur by apoptosis. These structural features contrast starkly with the cytologic changes observed when embryonic cells undergo necrosis (see Example 6).

EXAMPLE 2

Visualization of Cell Deaths in Fixed Tissues

Degenerating regions in fixed tissue preparations are readily identified with histological stains, including toluidine blue (TB) (Bowen and Lockshin, *Cell Death in Biology and Pathology*, (Chapman and Hall, New York), (1981); Fischbach and Technau, *Dev. Biol.* 104:219–239 (1984); Fristrom, *Molec. Gen. Genetics* 103:363–379 (1969); Murphy, *Dev. Biol.* 39:23–36 (1974); Giorgi and Deri, 1976). Previous studies with TB, however, made no clear distinction between apoptotic and necrotic forms of death, nor was it known whether the stain bound to the dying cells themselves or to cells or cellular substances associated with cell death, such as phagocytes. Applicants have examined the correspondence between the ultrastructural features of apoptotic cells described above and staining by TB. Semi-thin plastic sections of stage 13 embryos were stained with toluidine blue and examined by light microscopy using Nomarski optics. Ultrathin sections of adjacent tissue were examined in the electron microscope. In this way, Applicants were able to compare ultramorphology and staining properties of the same cell. In the light microscope, dying cells were distinguished as condensed figures, which become heavily stained with toluidine blue. Ultrastructural examination of the same region revealed that the chromophilic cells displayed obvious apoptotic features. It was noted that only the apoptotic corpses, but not the cytoplasm of the engulfing phagocytes were stained by toluidine blue. These results show that toluidine blue is a reliable stain for apoptotic cells in the Drosophila embryo. Furthermore, it appears that, in general, ultrastructural changes associated with cell death precede the changes which cause dying cells to become characteristically chromophilic to TB. In addition, this increased staining by TB appears to be specific for apoptotic forms of cell death, because necrotic cells remain unstained.

EXAMPLE 3

Visualization of Cell Deaths in Live Embryos

In order to investigate the pattern of programmed cell death throughout embryonic development, and as a prerequisite for genetic screens, Applicants developed a rapid and reliable way to visualize apoptotic cells in live Drosophila embryos. The method involves staining the embryos with either acridine orange (AO) or Nile blue (NB) while permeabilizing the waxy coat of the embryo with heptane. The embryos can then be viewed by conventional or confocal microscopy. By combining confocal microscopy with time lapse imaging, positive-staining cells can be followed for at least 30 minutes. The patterns of staining obtained in this fashion were found to closely resemble the distribution of pycnotic figures in toluidine blue stained plastic sections. There is an excellent correspondence between the position of brightly fluorescent cells stained with AO in whole mount embryos and the distribution of darkly stained degenerating figures in TB stained plastic sections.

Embryos stained with another vital dye, Nile blue (NB), display patterns which are identical to those seen with AO. Furthermore, simultaneous co-staining with these two dyes shows a precise correspondence between AO positive figures and NB positive figures.

Previous studies (Saunders, Science 154:604–612 (1962); Spreij, (1971)) did not resolve whether vital dyes label dying cells per se, or whether they merely provide an indicator of cellular activity associated with degeneration, such as phagocytosis (for example, see Savill et al., (1990). To achieve higher resolution of the structures that stain with the vital dyes and compare them to those that stain with toluidine blue after fixation, tissue spreads of the embryonic material were analyzed. Because specific staining with the vital dyes is compromised after fixation, the embryos were first stained in vivo with AO and then spread onto coated glass slides to dissociate the tissue. After photographically recording representative fields of tissue under fluorescence microscopy, these preparations were then fixed and stained with toluidine blue using standard histological procedures. In this fashion, the cytology of previously identified AO positive cells could then be reassessed by returning to the exact same field of tissue. The vast majority of toluidine blue positive cells were clearly positive for AO fluorescence. Under this higher resolution, a few cells were observed to be stained by either AO or toluidine blue but failed to be stained by both. Reasons for the occasional discrepancy between these staining procedures may include different dye affinity properties for cells at different stages of degeneration and/or losses of cells during the procedure. Nevertheless, these sequential comparisons established an excellent overall correspondence between cells that stained with AO in vivo and pycnotic cells that stained intensely with toluidine blue after fixation. Because toluidine blue stained figures are clearly apoptotic when examined by electron microscopy, these experiments establish that apoptotic cells in live Drosophila embryos are stained by the vital dyes AO and NB.

EXAMPLE 4

Vital Dyes Stain Both Unengulfed and Engulfed Cell Corpses

The analyses of TB stained plastic sections and electron micrographs showed that, in the Drosophila embryos, many apoptotic cells were engulfed by macrophage-like cells. To compare patterns of vital dye staining with the distribution of these engulfing cells, an additional marker specific for these macrophages was employed. The distribution of the macrophage marker was compared to the AO staining pattern in stage 13/14 embryos, and the two patterns were found to be remarkably similar. The coincidence between these staining patterns is particularly well illustrated at the leading edge of the dorsal epidermis during dorsal closure. This similarity persists during most embryonic stages, with the notable exception of late stages in central nervous system development, where prominent AO staining occurs in the absence of colocalizing hemocytes.

Double labelling experiments with the macrophage marker and toluidine blue also demonstrated the presence of TB stained apoptotic bodies inside many of the phagocytic cells. Only the portion of phagocytic cells, corresponding to those containing the apoptotic corpses, was stained by toluidine blue.

It is evident from these studies that AO and NB detect both free, i.e. unengulfed, and phagocytosed cell corpses. Close examination of whole mount and dissociated embryos stained with AO in vivo shows small, individual, uniformly fluorescent cells representing unengulfed apoptotic bodies. Cell corpses that have already been engulfed can be observed as discrete, vesicular staining bodies inside phagocytes. These experiments demonstrate that AO and NB, like toluidine blue, do not label macrophages directly. These cells are only labelled when they contain one or more engulfed apoptotic corpses, which are selectively stained by these dyes. Time lapse studies show that AO staining of dead cell corpses can persist for over 2 hours. Even in these advanced stages of cell death, the bright staining of these vital dyes is restricted to the engulfed cell corpses inside phagocytes. Finally, labelled corpses within macrophages are detected immediately upon staining of live embryos. Because the staining procedure takes only a few minutes, the majority, if not all, of the apoptotic corpses must have been engulfed prior to the AO treatment of embryos. This indicates that AO and NB are capable of staining apoptotic bodies after their engulfment and therefore, must be able to readily enter and penetrate live phagocytes.

EXAMPLE 5

Selectivity of Acridine Orange and Nile Blue

The selectivity of AO and NB for dying cells was examined by inducing an alternative form of cell death referred to as necrosis. Necrosis can be induced by exposing cells to various external injuries, such as oxygen deprivation (hypoxia), abnormal temperature (hypo- or hyperthermia), or certain toxins (reviewed in Wyllie, *Cell Death in Biology and Pathology* (eds. Bowen, I. D., and Lockshin, R. A.) (Chapman and Hall (1981); Kerr and Harmon, *Apoptosis: The Molecular Basis of Cell Death* (Tomei, L. D., and Cope, F. O.), (Cold Spring Harbor Laboratory Press, New York, pp. 5–29) (1991)). Necrotic deaths are characterized by a general swelling of the cell, mitochondrial dilation, loss of membrane integrity, and eventual plasma membrane rupture. This mode of death is dramatically distinct from apoptosis. To induce necrosis, Drosophila embryos were deprived of oxygen for a period of 4 hours and then examined by electron microscopy. Cells from these embryos exhibit the characteristic features of necrosis, including dilated mitochondria. When these embryos were stained with AO and observed in the green fluorescence channel, stage specific staining of apoptotic cells was generally preserved, yet an enhanced level of background nuclear staining tended to obscure these images. Observations of AO staining in the red (rhodamine) channel showed no ectopic AO staining, even though essentially every cell in these embryos suffered necrosis. Furthermore, embryos treated in this fashion retained the AO staining pattern reminiscent of the staining observed at the developmental stage during which necrosis was induced; this provided an internal control for these experiments. Similar results were obtained by staining plastic sections of these embryos with toluidine blue. Necrotic cells showed no significant increase in affinity for toluidine blue, and the stage-specific pattern of staining of apoptotic bodies was again preserved.

AO staining in vivo and TB staining of plastic sections, thus, show parallel properties with respect to necrotic tissue. Necrotic cells are apparently not recognized by these dyes under the described conditions. Furthermore, selective staining by these dyes is not merely a passive consequence resulting from compromised membrane permeability in dying cells, since apoptotic corpses inside phagocytes are readily labelled, indicating that these dyes readily enter and penetrate live cells. It is thus reasonable to conclude that biochemical changes characteristic of apoptotic forms of cell death are responsible for the selective affinity of apoptotic cells to AO and toluidine blue.

In contrast to AO, NB was found to stain apoptotic and necrotic cells indiscriminately under the same conditions.

EXAMPLE 6

Effect of Mutations and Environmental Factors on Apoptosis

The ability of vital dyes to detect ectopically induced cell death in mutants with perturbed embryonic development was assessed. Mutations at polyhomeotic cause extensive degeneration in the ventral epidermis (Dura et al., 1987; Smouse and Perrimon, 1990). Embryos mutant for polyhomeotic exhibited excessive AO staining in this region and elsewhere. Mutations at crumbs, which cause massive degeneration of epithelial tissue (Tepass et al., 1990), also display AO staining that is widespread throughout the epidermis. Similar results were obtained with NB.

The effect of environmental factors on apoptosis was also examined by exposing wild type embryos to various doses of X-irradiation, which, in other systems, has been shown to cause protein synthesis-dependent apoptosis (see, e.g., Umansky, *Apoptosis: The Molecular Basis of Cell Death* (eds. Tomei, L. D., and Cope, F. O.), (Cold Spring Harbor Press, New York) (1991); Tomei, *Apoptosis: The Molecular Basis of Cell Death* (Cold Spring Harbor Laboratory Press, New York) (1991)). When 3–4 hour old wild type embryos were exposed to a low does of X-rays (600 rads), no staining was noted immediately after irradiation. However, after aging these embryos for 7 hours of physiological time, an excessive number of AO positive cells was observed. Higher doses of X-irradiation (4000 rads) gave a more rapid and very noticeable increase of AO labelled dying cells that displayed the ultrastructural features of apoptosis. In fact, AO stained cells could be induced prior to the developmental stage at which the onset of cell death first appears. When 3–4 hour old embryos were irradiated at 4000 rads, aged for various times and then examined for AO staining, Applicants found that dying cells were readily observed at least 2 hours earlier than would otherwise normally occur. The appearance of precocious dying cells could be suppressed by cycloheximide treatments that immediately followed exposure to X-rays, suggesting that some aspect of irradiation-induced cell death is apparently dependent upon protein synthesis.

In a variety of contexts, it has been shown that cell death is an active process that can be blocked or delayed by inhibitors of protein synthesis (Tata, *Dev. Biol.* 13:77–94 (1966); Lockshin, *Apoptosis: The Molecular Basis of Cell Death* (eds. Tomei, L. D., and Cope, F. O.), (Cold Spring Harbor Laboratory Press, New York, p. 47–60) (1969); Fahrbach and Truman, *Soc. Neurosci. Abst.* 14:368 (1988); Martin et al., *J. Cell Biol.* 106:829–844 (1988); Oppenheim et al., *Dev. Biol.* 138:104–113 (1990)). The above cycloheximide inhibition experiments address this issue in the Drosophila embryo. Although very early treatments with cycloheximide prevented the appearance of AO stained cells, it was also clear that these treatments had imposed such general and widespread effects upon development that a meaningful assessment of the result was impossible. On the other hand, when cycloheximide was introduced at a later stage, shortly before the first onset of cell deaths, their occurrence was not affected. However, these results did show that X-irradiation induced cell deaths could be suppressed by cycloheximide treatment. The precocious cell deaths apparently depend upon some aspect of de novo protein synthesis. More direct evidence for the active nature of cell death in Drosophila comes from the identification of mutations that block all embryonic cell deaths (e.g., the H99 deletion).

These results demonstrate the utility of the vital dyes AO and NB as useful tools for investigating the effects of mutations and environmental factors, including chemicals, on programmed cell death in the Drosophila embryo. Due to the ease and speed of these assays, it should be possible to screen large numbers of embryos or tissues for the identification of mutations and chemicals and other factors.

EXAMPLE 7

Mapping of Cell Deaths During Embryogenesis

The pattern of apoptotic cell deaths occurring throughout Drosophila embryogenesis was mapped by staining live embryos with AO or NB and viewing them under confocal or fluorescence microscopy. The results of this study showed that a large number of cells die at many different times and in many different tissues and regions of the embryo. Although the distribution of dying cells changes dramatically during development, the pattern of cell death for any given developmental stage was remarkably reproducible.

Therefore, the induction of these deaths appears to be tightly controlled and to result from "natural" causes. Prior to and during their ingestion by macrophages, dying cells are often extruded from a developing organ or cell layer. Because detection of cell death with vital dyes includes these late stages of degeneration, patterns observed with AO or NB reflect the accumulation of corpses in phagocytes as well as the position of dying cells. Therefore, these observations do not necessarily reveal the precise original position of a dying cell. However, since the pattern of cell death is very reproducible for a particular developmental stage, it appears that the original position of a dying cell typically approximates the final position of its corpse.

Interestingly, in contrast to the situation in the nematode C. elegans (Sulston and Horvitz, 1977; Ellis et al., Annu. Rev. Cell Biol. 7:663–698 (1991)), at least some of the cell deaths in the Drosophila embryos do not appear to be strictly stereotyped. A detailed analysis of cell death in the Drosophila central nervous system (CNS) revealed significant asymmetries in the exact number and position of degenerating cells on either side of the midline. These differences are significant, because they are not easily explained either by subtle temporal variances or by relocation of dead cells upon phagocytosis in migratory cells. First, time-lapse studies demonstrate that apoptotic cells in the CNS retain AO-staining for at least 45 minutes, arguing strongly against small sporadic temporal differences as a potential explanation for the observations. Second, it is known, based on electron microscopy and labelling experiments, that circulating macrophages do not have access to degenerating cells within the CNS cell body layer. In this context, a dying cell is unlikely to wander far from its original position. Thus, it can be concluded that apoptotic deaths during the later stages of CNS development in the Drosophila embryo are not strictly predetermined, but that the decision to die is somewhat flexible.

This plasticity is probably influenced by signals from the local environment and/or the ability of a given cell to properly differentiate. The importance of cell-cell interactions for influencing cell death in the visual system of Drosophila has been well documented (Fischbach and Technau, Dev. Biol. 104:219–239 (1984); Steller et al., Cell 50:1139 (1987); Wolff and Ready, Development 113:825–839 (1991); Campos et al., Development 114:355–366 (1992)). Similar interactive processes may regulate cell survival during embryogenesis. Many mutations involved in embryonic development (see, e.g., Dura et al., 1987; Magrassi and Lawrence, Development 104:447–451 (1988); Tepass et al., (1990)) or imaginal development (Fristrom, Molec. Gen. Genetics 103:363–379 (1969); James and Bryant, 1981; Bonini et al., 1990) show ectopic cell death. Moreover, cell death in ftz mutants is not restricted to cells that would normally express this gene product (Magrassi and Lawrence, Development 104:447–451 (1988)). Hence, as is the case for many organisms, Drosophila also displays a capacity to eliminate cells that do not successfully complete their developmental program.

The following descriptive accounts are based on observations of embryos stained with AO and NB. It is important to keep in mind that these stains detect cell corpses that may have already fragmented into two or more apoptotic bodies. It is furthermore evident that one phagocyte may contain several stained corpses that might appear as a single stained structure. Finally, the continual disappearance of AO stained cells with time allows only dynamic snapshots of cell death patterns, potentially leading to a significant underestimate of the total number of cell deaths. For these reasons, it is difficult to derive an accurate numerical estimate by this method. Nevertheless, to provide an impression of the scope of this process during embryogenesis, numbers of AO stained figures are occasionally cited in the following descriptions. Because phagocytic cells do not circulate within the central nervous system, quantitation of AO stained figures in the ventral nerve cord are likely to represent a fairly accurate, stage-specific estimate of the number of cell deaths in this tissue.

Stage 11

No sign of cell death was detected until about 7 hours after egg laying (AEL). This time point corresponds to the later part of the fully extended germ band stage. The first dying cells are invariably observed in the dorsal region of the head just anterior to the extended tip of the germ band. Apoptotic cells are also observed inside the epidermal cell layer of the gnathal segments and near the caudal tip of the extended germ band.

Stage 12

As the germ band retracts during stage 12, cell death becomes far more widespread and prominent. During early germ band retraction, dying cells accumulate just beneath the developing epithelium of the gnathal segments, throughout the procephalic lobe region and within the interstitial space of the cylpeolabrum. As the retracting germ band reaches 50% egg length, cell death becomes more prominent within the most posterior abdominal segments, and early signs of degeneration along the ventral midline can be observed within the most anterior thoracic segments. Cell death in the dorsal cephalic region, just beneath the dorsal ridge, also becomes very prominent. Scattered cell deaths also begin to appear in a segmentally reiterated pattern within the lateral portions of the ventral region. Toward the completion of germ band retraction, cell death is very conspicuous in the ventral neurogenic region. It is interesting to note that the onset of cell death in this region does not occur simultaneously in all segments. Prominent numbers of dying cells first appear along the ventral midline in the thoracic and posterior abdominal segments, yet they are nearly absent from mid-abdominal segments. Cell death within the mid-abdominal segments occurs on a slightly later schedule and, as germ band retraction proceeds, the waves of cell death along the midline eventually converge to form one continuous line.

Stage 13

With the exception of the central nervous system, all major zones of degeneration have been fully established by the completion of germ band retraction. By this stage (about 9.5–10.5 hours AEL), cell death in the dorsal portion of the head becomes very prominent, as marked numbers of corpses accumulate around the supraoesophageal ganglia and beneath the dorsal ridge. Noticeable accumulation of corpses has also occurred within the cylpeolabrum and just anterior of the salivary duct.

As this stage progresses, scattered and variable numbers of cell deaths are evident throughout the dorsolateral epidermis. In addition, segmentally reiterated AO staining in the ventrolateral portions of the epidermis becomes very prominent. Clusters of AO positive cells accumulate along the midline, which are clearly associated with phagocytic macrophages. Lateral to the midline, up to 30 AO positive figures appear at a slightly later point in stage 13 and are scattered throughout the most ventral portion of each hemisegment. The vast majority of dying cells in this region accumulate in the interstitial spaces between the ventral epidermis and the nerve cord. It is difficult to determine whether these corpses originated from cells that were committed to neural or epidermal fates. By the end of this stage, the pattern of cell death in the ventrolateral region gradually evolves into one central and two lateral columns of macrophage associated staining along this portion of the embryo. The portion of cells in the central, midline column is fairly consistent among the segments, whereas the lateral columns, although also segmented in character, tend to show more variably positioned cell death figures.

Stage 14

The AO and NB staining cells generally tend to persist from the previous stages, especially along the ventral midline and in the head region. As this stage progresses (about 10.5–11.5 hours AEL), a new and continuous ring of dying cells becomes evident at the leading edge of the dorsally closing tissue during gut closure. At this stage, degenerating cells are rapidly phagocytosed by neighboring macrophages.

Stage 15

Once dorsal closure is complete (about 13 hours AEL), the general domains of vital dye staining from earlier stages fade, and sporadic cell deaths occur throughout the body cavity. Many of these dying cells are localized just inside of the body wall or around the mid-gut. The appearance and position of this staining pattern suggests an association with phagocytic macrophages. Toward the end of this stage, cell death begins to occur in the condensing central nervous system.

Stage 16

As the nerve cord condenses (about 14 hours AEL), large numbers of cell deaths can be observed with vital dyes throughout the central nervous system (e.g., within the brain and the ventral nerve cord). At this stage, neuromuscular development matures to the extent that twitching movements can be observed. Phagocytic hemocytes do not invade the tightly packed cell body layer of the central nervous system (CNS) and, hence, unlike cell deaths in other regions, no engulfment by circulating macrophages occurs in this region. The pattern of vital dye staining in the CNS should therefore most accurately reflect the precise position and numbers of apoptotic cells. AO staining within the ventral nerve cord was analyzed by superimposing optical sections that extend through this portion of the CNS. These analyses result in a graphic summation of cell death through the entire depth of the ventral cord. Using this technique in combination with time-lapse preparations, many AO positive cells in the CNS have been followed for up to 45 minutes. For example, of the approximately 140 AO stained cells in the condensed ventral nerve cord, most are positioned at the anterior and posterior termini. Approximately 140 AO positive cells were detected at this stage. At a slightly earlier stage, cell death is more uniformly distributed over the length of the ventral cord and appears segmentally reiterated. A similar pattern of degeneration has been reported during late embryogenesis in the CNS of Calliphora (Starre-van der Molen, 1974).

Comparative analyses of AO staining on either side of the midline reveals an overall symmetry in the pattern of cell deaths in the condensing ventral nerve cord. Although the precise number and position of AO stained cells may vary, cell death on one side of the ventral midline is often accompanied by a similarly positioned dying cell(s) on the opposite side of the midline. There are, however, clear instances of asymmetric cell deaths in the nervous system as well. That is, AO positive cells are not always accompanied by a similarly positioned dying cell(s) on the opposite side of the midline. These asymmetries are more readily observed at later stages of ventral nerve cord maturation, when neural cell death is somewhat less prominent. Because acridine staining can persist for relatively long periods in these preparations (at least 45 minutes), sporadic variances of a temporal nature are unlikely to be the entire cause for asymmetric staining. Bilateral symmetry in the developing nerve cord normally extends to the level of cell age and identity (for example, Campos-Ortega and Hartenstein, *The Embryonic Development of Drosophila melanogaster* (Springer Verlag, New York) (1985); Doe et al., (1988); Klämbt et al., (1991)). It is therefore plausible that asymmetric cell deaths in the nerve cord reflect some general degree of plasticity regarding the exact number and position of cells that die during CNS development in the embryo.

Summary of Cell Death During Drosophila Embryogenesis

The earliest appearance of cell death is observed in the dorsal cephalic region, within the gnathal segments and in the cylpeolabrum as the germ band begins to retract (stage 11). Thereafter, as germ band retraction proceeds (stages 12 and 13), cell death becomes widespread throughout the embryo, particularly in the ventrolateral portions and around the procephalic lobes. Large numbers of degenerating cells accumulate in the interstitial spaces beneath the dorsal ridge, along the ventral midline and within the gnathal segments. During dorsal closure, a zone of degenerating cells, organized in the shape of a ring, forms around the closing dorsal tissue (stage 14). As head involution becomes well advanced (stage 15), zones of vital dye staining from earlier stages subside, and scattered subepidermal staining appears throughout the embryo. Eventually, prominent cell death appears throughout the CNS as the ventral nerve cord condenses (stage 16). In contrast to earlier stages, cell death in the cell body layer of the ventral cord and brain hemispheres at this time is not associated with phagocytic hemocytes.

It is apparent from these studies that a large number of cells die at many different times, and in many different tissues and regions of the embryo. These methods of imaging cell death, however, do not readily allow for a precise census of the number of cell deaths in most contexts. There are several limitations to the use of AO and NB as a means to count cell deaths. First, dying cells can fragment into multiple AO stained apoptotic bodies. Second, most of the dying cells are rapidly engulfed by phagocytes. A single phagocyte usually contains multiple cell corpses that are labelled by AO and NB, but may appear as a single stained structure. Finally, the continual loss of cells that were "pulse-stained" over time means that these methods provide only a static snap-shot image of a very dynamic process. Nevertheless, a reasonable numerical assessment of cell deaths can be made in the ventral nerve cord, since bilateral symmetry of cellular age and identity is generally well preserved throughout the Drosophila central nervous system (for example, see Campos-Ortega and Hartenstein, *The Embryonic Development of Drosophila melanogaster* (Springer Verlag, New York) (1985)); Doe et al., (1988); Klämbt et al., (1991)). Assuming that there are approximately 300 cells in each segment at this stage (Poulson, (1950); Truman and Bate, *Dev. Biol.* 125:145–157 (1988)), it is estimated that at least 4% of this neural population undergoes programmed cell death. Because these counts derive from static rather than cumulative images, this number represents a very conservative estimate.

EXAMPLE 8

Egg Collection and Embryo Staging

Wild type (Canton S) eggs were collected on molasses/agar plates, either at 25° C. or at 18° C., and staged according to Campos-Ortega and Hartenstein (1985). Tightly staged populations of embryos were prepared by sorting blastoderms on the basis of their characteristic morphology. Embryos from stock of polyhomeotic[505] (Dura et al., (1987)) and crumbs[11A22] (Tepass et al., (1990)) were also analyzed.

EXAMPLE 9

Staining with Vital Dyes

Embryos were dechorionated with 50% bleach, rinsed with water and placed in an equal volume of heptane and either 5 µg/ml of acridine orange (Sigma) or 100 µg/ml Nile blue A (Sigma) in 0.1 M phosphate buffer, pH about 7.2. After 5 minutes of shaking, embryos were removed from the interface and placed under series 700 Halocarbon oil (Halocarbon Products Corp., Hackensack, N.J.). Samples were viewed either with a conventional fluorescence microscope or with an MRC confocal scanning laser microscope (Bio-Rad), using a BHS color cube filter to detect green fluorescence or a YHS color cube filter to detect red fluorescence. Acridine stained embryos can be viewed with filters for either green or red fluorescence, and in general, these patterns are very similar. Confocal image processing was performed either with software provided by the manufacturer or with the Voxel View (Vital Images, Iowa) program on a Silicon Graphics computer. For time lapse studies, acridine stained embryos were placed under Voltalef oil (3s or 10s) on petri-perm dishes (Bachofer, Reutlingen, Germany).

EXAMPLE 10

Fixed Tissue Spreads

Embryos were stained with acridine orange as described above, washed in phosphate buffer to remove heptane and individually placed on slides coated with 0.5% gelatin and 0.05% chrom alum. A siliconized cover slip placed over the embryo was used to gently spread the tissue into a monolayer. After photographic recordings of representative fields, the slides were rapidly frozen at −70° C. To fix the tissue, the cover slip was quickly removed, and slides were rapidly submerged in 2.5% glutaraldehyde for 20 minutes. For toluidine blue staining, glutaraldehyde fixed tissue was placed in 1% osmium tetroxide for 5 minutes, washed with water, air dried and then stained with a solution of 0.1% toluidine/0.1% sodium borate for 5 minutes at 55° C.

EXAMPLE 11

Electron Microscopy.

Dechorionated embryos were shaken in equal volumes of heptane and a fixative solution of 1.5% acrolein, 1% paraformaldehyde, 2% glutaraldehyde in 0.1M phosphate buffer, pH 7.0, for 20 minutes. Embryos were then freed of the surrounding vitelline membranes by hand dissection in 0.1M phosphate buffer, pH 7.0, (PB) and refixed for another 30 minutes in the above fixative solution. After several washes in PB, the embryos were treated with a 2% solution of osmium tetroxide in PB for 1 hour. Following several washes in PB the embryos were dehydrated through an ethanol series, washed in several changes of propylene oxide and then embedded in Spurr's media (Polysciences, Warrington, Pa.; Spurr, 1969). Alternatively, after osmium fixation, some embryos were washed in water and then incubated in 1% uranyl acetate (in water) at 50° C. for 12–16 hours. Thin sections from these samples were viewed directly by electron microscopy without any subsequent staining. Thin sections from whole mount samples that had not been stained with uranyl acetate were stained with uranyl acetate and lead citrate according to Osborne (1980). For light microscopy, sections were stained with 0.01% toluidine/0.05% sodium borate with or without 0.05% methylene blue at 55° C. for approximately 5 minutes.

EXAMPLE 12

Irradiation of Embryos

Three to four hours after egg laying (AEL), Canton S embryos were exposed to 600 or 4000 rads of X-irradiation using a Torrex 120D X-ray inspection system (Astrophysics Research Corp., California). Irradiated embryos were allowed to age for another 14 hours at 18° C. Compared to a hatching frequency of $\geq 290\%$ for untreated embryos, these protocols of X-irradiation reduced the hatching frequency to about 5% for a 600 rad exposure or 0% for a 4000 rad exposure. Some embryos irradiated at 4000 rads were treated with cycloheximide immediately afterward, by shaking them in heptane and 10 µg/ml cycloheximide (in 0.1M phosphate buffer). These embryos, along with mock treated samples, were aged for various times under Voltalef oil.

EXAMPLE 13

Hypoxia Treatments

Ten to 12 hours AEL embryos were dechorionated and placed under heptane for 4 hours. Survival after this treatment is 0% (no hatched embryos observed out of 400 scored). Embryos subjected to this treatment were either stained with vital dyes or prepared for electron microscopy.

EXAMPLE 14

Analysis of Deletion Mutants, Mapping of the rpr Transcript and Sequencing of rpr DNA Embryos deleted for chromosomal region 75C1,2 lack almost all the apoptotic cell deaths observed in wild type embryos. Deletion stocks provided by the Bloomington stock center were screened for cell death by AO staining (Abrams et al., *Development* 117:29–44 (1993)). The majority (83 strains or 65%) of these deletions did not significantly affect the amount of cell death in embryo. Twenty six deletion strains (20%) gave a significant number of progeny that had excess AO staining. A smaller number (17 strains or 13%) showed a decrease in the number of AO staining cells. Three overlapping deletions (2%), Df(3L)WR4, Df(3L)WR10 (Segraves and Hogness, *Genes & Development* 4:204–219 (1990)), and Df(3L)Cat$^{DH104}$ (Mackay and Bewley, *Genetics* 122:643–652) (1989)), showed at most one or two AO positive cells (much less than 1% of wild-type levels) at all times during development. A fourth deletion, hid$^{H99}$, showed a similar phenotype and lies entirely within the overlap of the above deletions.

Embryos were fixed and sectioned for electron micrography as described above. Mutant embryos were identified on the basis of their AO phenotype prior to fixation. The circulating cells within the subepidermal spaces of both wild-type and mutant embryos are macrophages, which express macrophage specific markers. In mutant embryos, these cells are smaller than in wild type, since they lack apoptotic corpses.

EXAMPLE 15

Embryos Which Lack Cell Death

Embryos which lack cell death have extra cells. A) Central nervous system of wild type embryo stained with elf-1 antibody. For elf-1 antibody staining, the central nervous system was dissected from fully developed wildtype, and Df(3L)hid$^{H99}$ homozygous embryos. The nervous systems were fixed in 2% paraformaldehyde in 0.1M phosphate buffer for 20 minutes at room temperature. The nervous systems were washed and blocked, and incubated in the elf-1 antibody overnight at 4°. They were washed and incubated with FITC conjugated second antibody at 4° overnight. The antibody staining was imaged on a confocal microscope, and a series of images were summed to give a complete picture of the staining throughout the ventral cord. The arrow in A and B mark the approximate boundary between the thoracic and abdominal neuromeres. Approximately six cells stain in each abdominal neuromere. B) Central nervous system of a fully developed hid$^{H99}$ homozygous embryo. These embryos can be easily distinguished from their heterozygous siblings by the abnormal cephalopharyngeal skeleton (Abbott, M. K. and J. A. Lengyel, *Genetics* 129:783 (1991)). Mutant embryos contained more than 20 cells in some of the abdominal neuromeres. This result is consistent with the continued survival of the abdominal neuroblasts in the mutant embryos. Scale bars in A and B are 10 μm. C) Kr antibody staining of a stage 16 wild type embryo. At this stage, the Kr antibody stains a subset of cells in the central nervous system, as well as cells in the larval photoreceptor organ (arrow) (Gaul, U. et al., *Cell* 50:639 (1987)). D) Kr antibody staining of a stage 16 homozygous hid$^{H99}$ embryo. There are many more Kr-positive cells in the central nervous system of mutant embryos. For example, the number of Kr-positive cells in three neuromeres ranged from 159 to 189 in wild type embryos, as opposed to 364 to 445 in the same neuromeres of homozygous hid$^{H99}$ embryos. There also appear to be more cells in the larval photoreceptor organ (arrow). Scale bars in C and D are 50 μm. E) Higher magnification of the ventral cord of a wild type embryo stained with the Kr antibody. F) Kr antibody staining of the ventral cord of a homozygous hid$^{H99}$ embryo of a similar age. Again note the increased number of cells. Scale bars in E and F are 20 μm.

EXAMPLE 16

A Cosmid Transgene Containing the rpr Transcription Unit Restores Apoptosis

A cosmid containing approximately 25 Kb genomic DNA from position ~260 of FIG. 1 was introduced into embryos by P element-mediated transfer. Reuben and Spradling, *Science* 218:343–353 (1982). A significant number of cells stained positively with acridine orange in the presence of the transgene, indicating that apoptosis had been restored. In mutants lacking rpr, no staining was evident.

EXAMPLE 17

Drosophila Libraries

The following Drosophila libraries were used in the work described herein.

1. *Drosophila melanogaster* Cosmid Library Construction of the cosmid library

The library was constructed using fairly standard techniques. Two features of the library are somewhat unusual however, the vector and the source of the genomic DNA.
The NotBamNot-CoSpeR cosmid vector:

The vector is a modified form of CoSpeR, a cosmid vector (built in the laboratory of Dr. V. Pirotta) that may be used for the P-element mediated germ-line transformation of *Drosophila melanogaster*. This vector contains the white gene as a marker and is thus convenient to use as a transformation vector. To make the library easier to use, Dr. Renate Deuring and I modified this vector in several ways prior to making the cosmid library. We deleted part of the polylinker in the vector and introduced Not1 sites flanking the BamH1 cloning site. The new vector, NotBamNot-CoSpeR (see accompanying map) has several features that simplify the analysis of recombinant cosmids (these features are discussed later).
Source of *Drosophila melanogaster* genomic DNA:

The second unusual feature of the library is the source of the genomic DNA. We have observed that the presence of polymorphisms in stocks used to build genomic libraries often causes problems with the mapping and analysis of genomic clones. These problems become quite significant in the analysis of the large inserts contained in cosmids. Furthermore, many cDNA and genomic libraries are made from different stocks (Canton S, Oregon R, etc.). This often makes the direct comparison of cDNA and genomic clones impossible. Since we planned on making a variety of new cDNA and genomic libraries, Dr. Jim Kennison undertook the construction of a stock (iso-1) isogenic for all four chromosomes. A diagram of how this stock was made is enclosed. The stock bears the recessive visible markers y, cn, bw, and sp. This facilitates the detection of stock contamination. The iso-1 strain is available upon request.
Preparation of insert DNA:

The insert DNA was made by partially digesting iso-1 genomic DNA with Sau3A and isolating 30–45 kilobase fragments on sucrose gradients. Prior to cloning, the insert DNA was treated with phosphatase to prevent any possible "scrambling" of inserts during the subsequent ligation to vector DNA. This step should be unnecessary given the size-selection of the insert DNA, but was carried out as an additional precaution.
Preparation of vector DNA:

CsCl-banded NotBamNot-CoSpeR DNA was cut with Hpa1 and treated with phosphatase. This cut the vector between two of its three cos sites. The DNA was then digested with BamH1 to generate two Hpa1/BamH1 vector fragments equivalent to phage arms.
Ligation and packaging of the library:

Vector and insert DNA were ligated at a concentration of 40 and 86 ng/μl respectively. The ligated DNA was packaged in vitro, diluted in phage dilution buffer in 7% DMSO, and stored at −80° C. To titer the library, a HB101 plating stock was infected with packaged cosmids and grown for one hour in L-broth lacking antibiotic. the cells were then titered on plates containing 40 μg/ml ampicillin to determine the number of transformants present.
Amplification of the library:

Approximately 2.7×10⁶ packaged cosmids were used to infect HB101. The transformants were allowed to grow for one hour in 100 ml of L-Broth before ampicillin was added to 40 μg/ml. The culture was then grown for another 9.5 hours before DMSO was added to 7% and the library was aliquoted, frozen in liquid nitrogen and stored at −80° C. This procedure resulted in a 30,000 fold amplification of the library. This represents a quantity sufficient for two million independent screening of the library.

2. *Drosophila melanogaster* (iso-1) embryonic cDNA library:

This library is described in Tamkun et al., *Proc. Natl. Acad. Sci., USA* 88:3120–3124 (1991). The source of RNA was 0–24 hour embryos. The vector used was λgt11. More than 600,000 independent recombinants were amplified. The original titer of the amplified library was $7.8 \times 10^8$ pfu/ml (70% recombinant). The current titer may be lower; I recommend titering the library before use. Y1090 should be used as the host for screening the library. This strain contains a plasmid (conferring ampicillin resistance) encoding a gene that overproduces lac repressor in the host cell. This prevents selection against clones that produce fusion protein. Although the cDNA was not size selected before cloning, the average insert size appears to be relatively high. Inserts can be excised with EcoR1.

3. *Drosophila melanogaster* (iso-1) genomic phage library:

This library was constructed in λEMBL3 according to the methods described in Tamkun et al., *Proc. Natl. Acad. Sci., USA* 81:5140–5144 (1984). Inserts were prepared by partial digestion with Sau3A, size fractionation on sucrose gradients and treatment with calf intestinal phosphatase. The average insert size is 19 kb. The library is greater than 99& recombinant. More than 500,000 independent recombinants were amplified. The recommended host is LE392. To our knowledge, the library contains no "holes" or scrambled inserts.

EXAMPLE 18

Analysis of the Central Nervous System in $hid^{H99}$ Embryos

For elf-1 antibody staining, the central nervous system was dissected from fully developed wild type and $hid^{H99}$ homozygous embryos. The latter were identified by their failure to undergo head involution. The nervous systems were fixed in 2% paraformaldehyde in 0.1M phosphate buffer, pH 7.5, for 20 minutes at room temperature, and stained with the elf-1 antibody as previously described (Bray et al., *Genes & Development* 3:1130–1145 (1989)). An FITC-conjugated second antibody was used. The antibody staining was imaged on a confocal microscope, and a series of images were summed to give a complete picture of the staining through the ventral core. Kr staining was done as previously described (Gaul et al., *Cell* 50:639–647 (1987)).

With the elf-1 antibody, approximately six cells were observed to stain in each abdominal neuromere in wild type embryos. In contrast, $hid^{H99}$ homozygous embryos contained more than 20 cells in some of the abdominal neuromeres. The $hid^{99}$ homozygous embryos can be easily distinguished from their heterozygous siblings by an abnormal cephalopharyngeal skeleton (Abbott and Lengyel, *Genetics* 129:738–739 (1991)).

The Kr antibody stains a subset of cells in the central nervous system, as well as nuclei of the larval photoreceptor organ (Gaul et al., *Cell* 50:639–647 (1987)). Kr antibody staining of a stage 16 homozygous $hid^{H99}$ embryo showed many more Kr-positive cells in the central nervous system than in wild-type embryos. There also appear to be more larval photoreceptor neurons. Kr antibody staining of the ventral cord of a homozygous $hid^{H99}$ embryo also showed an increased number of cells than in wild-type embryos of a similar age.

EXAMPLE 19

Analysis of X-irradiated $hid^{H99}$ Embryos

As the effect of irradiation on embryos is known to vary during development (Wurgler and Ulrich, *The Genetics and Biology of Drosophila* 1C (eds. Ashburner, M. and Novitski, E.), (Academic Press, New York) (1976)), it was important to insure that the treated embryos were as homogeneous in age as possible. Embryos were collected from CS or $hid^{H99}$/TM 3 stocks and selected at blastoderm stage by morphology. These embryos were then aged under Voltalef oil (Atochem) for an additional 1.5 hours and then irradiated with 4000 rads in a Torrex 120D X-ray machine. Embryos were aged for a further 14 to 18 hours at 18° C., and subsequently stained with AO, or fixed and processed for EM as described above. Mutant embryos can be easily differentiated from wild-type embryos, as they contain many fewer apoptotic cells. Results indicate that mutant embryos are capable of undergoing all of the events associated with apoptosis, from nuclear condensation to engulfment.

EXAMPLE 20

Expression of the rpr Gene

Expression of the rpr gene corresponds to the pattern of programmed cell death in the Drosophila embryo. Single stranded RNA probes generated from the rpr cDNA clone were used for in situ hybridization to whole mount embryos. The rpr transcript was shown to be present in the same regions of the embryo in which cell death later occurs, for example in the dorsal head, gnathal segments, and scattered cells in the abdominal segments of the stage 13 to 14 embryos. The diffuse staining in AO stained embryos is autofluorescence of the yolk. In older embryos both rpr transcription and AO staining are almost entirely restricted to cells in the central nervous system. Scale bars are 45 um.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. Isolated and purified DNA having a nucleotide sequence selected from the group consisting of:
   a) rpr cDNA having the nucleotide sequence of SEQ ID NO:1;
   b) rpr cDNA having the nucleotide sequence of SEQ ID NO:3;
   c) hid genomic DNA having the nucleotide sequence of SEQ ID NO:4;
   d) hid cDNA having the nucleotide sequence of SEQ ID NO:6;
   e) DNA encoding a cell death gene which hybridizes at 42° C. in 30% formamide, 5×SSC, 0.1% SDS and 5×Denhardt's Solution to DNA having a complementary nucleotide sequence of SEQ ID NO. 4; and
   f) DNA encoding a cell death gene which is detected with primers having the nucleotide sequences of SEQ ID NO:11 and 13.

2. Isolated RNA encoded by the DNA of claim 1.

3. Isolated and purified DNA encoding a protein having an amino acid sequence selected from the group consisting of:
   a) the amino acid sequence of SEQ ID NO. 2;
   b) the amino acid sequence of SEQ ID NO. 5;
   c) the amino acid sequence of SEQ ID NO. 7.

4. Isolated RNA transcribed from the DNA of claim 3.

5. An expression vector containing heterologous DNA that is operatively linked to expression control sequences and selected from the group consisting of:
   a) rpr cDNA having the nucleotide sequence of SEQ ID NO:1;
   b) rpr cDNA having the nucleotide sequence of SEQ ID NO:3;
   c) hid genomic DNA having the nucleotide sequence of SEQ ID NO:4;
   d) hid cDNA having the nucleotide sequence of SEQ ID NO:6;
   e) DNA encoding a cell death gene which hybridizes at 42° C. in 30% formamide, 5×SSC, 0.1% SDS and 5×Denhardt's Solution to DNA having a complementary nucleotide sequence of SEQ ID NO. 4;
   f) DNA encoding a cell death gene which is detected with primers having the nucleotide sequences of SEQ ID NO:11 and 13.

6. A host cell containing the expression vector of claim 5.

* * * * *

UNITED STATES PATENT AND TRADEMARK OFFICE
CERTIFICATE OF CORRECTION

PATENT NO. : 5,593,879
DATED : January 14, 1997
INVENTOR(S) : Hermann Steller, John M. Abrams, Megan E. Grether and Kristin White It is certified that error appears in the above-identified patent and that said Letters Patent is hereby corrected as shown below:

Column 1, lines 5-10, please delete the entire Funding section:

"Funding

This work is supported in whole or in part by the Howard Hughes Medical Institute, Pew Scholars Award, the American Cancer Society and the National Institutes of Health. The United States Government has certain rights in the invention."

Signed and Sealed this

Eighteenth Day of January, 2000

*Attest:*

Q. TODD DICKINSON

*Attesting Officer*  *Commissioner of Patents and Trademarks*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
    ( A ) LENGTH: 798 base pairs
    ( B ) TYPE: nucleic acid
    ( C ) STRANDEDNESS: unknown
    ( D ) TOPOLOGY: unknown ( i i ) MOLECULE TYPE: cDNA ( x i ) SEQUENCE DESCRIPTION: SEQ ID NO:1:

```
AATCATTGAA  TAAGAGAGAC  ACCAGAACAA  AGTGAACGAA  CTCGAAAATA  CGAAAGCAAA     60
GTGTGTGCGC  CAGTAACAAA  GAACTAACTC  GATAAATATT  CATTGTGCAG  AAGAGAAAGT    120
TATTGAGTCA  CTACCAGTTG  TGTAATTCCG  AACGAGAAGA  AAGATAAACC  AACAACAATG    180
GCAGTGGCAT  TCTACATACC  CGATCAGGCG  ACTCTGTTGC  GGGAGGCGGA  GCAGAAGGAG    240
CAGCAGATTC  TCCGCTTGCG  GGAGTCACAG  TGGAGATTCC  TGGCCACCGT  CGTCCTGGAA    300
ACCCTGCGCC  AGTACACTTC  ATGTCATCCG  AAGACCGGAA  GAAAGTCCGG  CAAATATCGC    360
AAGCCATCGC  AATGAGGATT  CGAGTAACTA  ACAAATACGG  GGAAAACCAA  TAGTCCAGTC    420
CAAAATCCAG  AGTACAAAGG  AAATAAGCAT  GAGCCAACCC  AAAACCCAAA  CACGTCACCA    480
CTCATCAGCC  GACGGCACTC  GATTTCTACT  GCAGTCAAGG  ACACAGAGCC  ACAACACCCA    540
CCCAATTTTA  GTTTACTCAT  CAAAGCGATT  GTGATAATGG  TTTTGTTTCT  ACAAAAAAGC    600
GGAGGAAAAA  TTTGAAAAAA  ATAACGTTTT  TATAAAGTCC  CCAATTTTTT  ACAAAAATGT    660
TTTAATGATA  TAAATCAACT  TTTTTAGAAA  TAATTTACTC  TTAAAGCCTA  TTTAAATGAA    720
TTACTACTGT  AATAGTTTGT  AAGTTCTTTT  TGTAAGACGA  GTTTTCTAA   GTTTTTTAA    780
GAAGAAACCC  CAGAAAAA                                                      798
```

( 2 ) INFORMATION FOR SEQ ID NO:2:

( i ) SEQUENCE CHARACTERISTICS:
        ( A ) LENGTH: 65 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

```
Met  Ala  Val  Ala  Phe  Tyr  Ile  Pro  Asp  Gln  Ala  Thr  Leu  Leu  Arg  Glu
 1                    5                      10                         15

Ala  Glu  Gln  Lys  Glu  Gln  Gln  Ile  Leu  Arg  Leu  Arg  Glu  Ser  Gln  Trp
                20                      25                    30

Arg  Phe  Leu  Ala  Thr  Val  Val  Leu  Glu  Thr  Leu  Arg  Gln  Tyr  Thr  Ser
          35                      40                         45

Cys  His  Pro  Lys  Thr  Gly  Arg  Lys  Ser  Gly  Lys  Tyr  Arg  Lys  Pro  Ser
     50                     55                       60

Gln
65
```

( 2 ) INFORMATION FOR SEQ ID NO:3:

( i ) SEQUENCE CHARACTERISTICS:
        ( A ) LENGTH: 94 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:3:

```
CGGGAGGCGG  AGCAGAAGGA  GCAGCAGATC  CTCCGCTTGC  GGGAGTCCCA  GTGGAGATTC     60
```

```
CTGGCCACCG TTGTCCTGGA AACGCTGCGC CACT                                    94
```

( 2 ) INFORMATION FOR SEQ ID NO:4:

( i ) SEQUENCE CHARACTERISTICS:
        ( A ) LENGTH: 1084 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

```
TCTGCCGACG TCGCGGTAGA GGCTCTGTTG CCGTAGTTTG AGGCCCCAGN GCGAACAGTT        60
CATTTTTAGC CGCGGAGCCA GTAAGACGTG TTTCCTGCCC TCTTTCTTTG AGTCTGCGAC       120
ACGTTTTAAG TGCTCTTCCA TAATTGACAA CAGCAAAAGC AAAGAATAAA AAAATAACAA       180
AAAATAAAAA ACGAAATCCA TCGTGAACAG TTTTGTGTTT TTAAATCAGT TCTAAACACG       240
AAAAGGGTTG ATGAAAAACG CAGAAGAATC CGAAAAACTA ACTAACCGAG CAAAAACTTG       300
ACTTGAGTGT TGTTTGACAA ATCAGGAAAG ATAAAAAACA AATCATAAGA AAAAACTGCA       360
CGAAAAATGA AAAGTTTCT AATATTCAAA ATCTTGCACA AGAAATACAA AATCAATTAA        420
AGTGAACTCT AACCAAAAGT TGTACACAAA ATAAAAAGCA AACAAAGCA GCGAAGAACA        480
ATCACAAGAA GAGCAAAGTG CCAACAAAGT GCAGGAAGGA AGGAAGCGGA TAAGGACAAA       540
AAGGAAGCCA GCACACACAC ACACACACCC ACACAATGGC CGTGCCCTTT TATTTGCCCG       600
AGGGCGGCGC CGATGACGTA GCGTCGAGTT CATCGGGAGC CTCGGGCAAC TCCTCCCCCC       660
ACAACCACCC ACTTCCCTCG AGCGCATCCT CGTCCGTCTC CTCCTCGGGC GTGTCCTCGG       720
CCTCCGCCTC CTCGGCCTCA TCTTCGTCCT CCGCATCGTC GGACGGCGCC AGCAGCGCCG       780
CCTCGCAATC GCCGAACACC ACCACCTCGT CGGCCACGCA GACGCCGATG CAGTCTCCAC       840
TGCCCACCGA CCAAGTGCTA TACGCCCTCT ACGAGTGGGT CAGGATGTAC CAGAGCCAGC       900
AGAGTGGTAA GTCTACAAAG ATCTCAATTC TCCACTCTTA AGAACTTTGA AATTGTGTGG       960
GTTAATCAGG ATATCCATTT AGTTTACCTC AAATACATTT GCAGATACAA AAATAAGCTT      1020
TTCGATTCAT ATACGGTTAT TAATTGCGAA ATGTTTAACG TAAGTTCCCA CACAGAATAA      1080
CGTC                                                                  1084
```

( 2 ) INFORMATION FOR SEQ ID NO:5:

( i ) SEQUENCE CHARACTERISTICS:
        ( A ) LENGTH: 410 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:5:

```
Met  Ala  Val  Pro  Phe  Tyr  Leu  Pro  Glu  Gly  Gly  Ala  Asp  Asp  Val  Ala
 1               5                    10                        15

Ser  Ser  Ser  Ser  Gly  Ala  Ser  Gly  Asn  Ser  Ser  Pro  His  Asn  His  Pro
                20                    25                        30

Leu  Pro  Ser  Ser  Ala  Ser  Ser  Ser  Val  Ser  Ser  Ser  Gly  Val  Ser  Ser
           35                        40                    45

Ala  Ser  Ala  Ser  Ser  Ala  Ser  Ser  Ser  Ser  Ala  Ser  Ser  Asp  Gly
      50                        55                    60

Ala  Ser  Ser  Ala  Ala  Ser  Gln  Ser  Pro  Asn  Thr  Thr  Thr  Ser  Ser  Ala
```

|  |  |  |  | 65 |  |  |  |  | 70 |  |  |  |  | 75 |  |  |  |  | 80 |
|---|---|---|---|---|---|---|---|---|---|---|---|---|---|---|---|---|---|---|---|
| Thr | Gln | Thr | Pro | Met<br>85 | Gln | Ser | Pro | Leu | Pro<br>90 | Thr | Asp | Gln | Val | Leu<br>95 | Tyr |
| Ala | Leu | Tyr | Glu<br>100 | Trp | Val | Arg | Met | Tyr<br>105 | Gln | Ser | Gln | Gln | Ser<br>110 | Ala | Pro |
| Gln | Ile | Phe<br>115 | Gln | Tyr | Pro | Pro<br>120 | Ser | Pro | Ser | Cys | Asn<br>125 | Phe | Thr | Gly |
| Gly | Asp<br>130 | Val | Phe | Phe | Pro<br>135 | His | Gly | His | Pro | Asn<br>140 | Pro | Asn | Ser | Asn | Pro |
| His<br>145 | Pro | Arg | Thr | Pro | Arg<br>150 | Thr | Ser | Val | Ser | Phe<br>155 | Ser | Ser | Gly | Glu | Glu<br>160 |
| Tyr | Asn | Phe | Phe | Arg<br>165 | Gln | Gln | Gln | Pro | Gln<br>170 | Pro | His | Pro | Ser | Tyr<br>175 | Pro |
| Ala | Pro | Ser | Thr<br>180 | Pro | Gln | Pro | Met | Pro<br>185 | Pro | Gln | Ser | Ala | Pro<br>190 | Pro | Met |
| His | Cys | Ser<br>195 | His | Ser | Tyr | Pro | Gln<br>200 | Gln | Ser | Ala | His | Met<br>205 | Met | Pro | His |
| His | Ser<br>210 | Ala | Pro | Phe | Gly | Met<br>215 | Gly | Gly | Thr | Tyr | Tyr<br>220 | Ala | Gly | Tyr | Thr |
| Pro<br>225 | Pro | Pro | Thr | Pro | Asn<br>230 | Thr | Ala | Ser | Ala | Gly<br>235 | Thr | Ser | Ser | Ser | Ser<br>240 |
| Ala | Ala | Phe | Gly | Trp<br>245 | His | Gly | His | Pro | His<br>250 | Ser | Pro | Phe | Thr | Ser<br>255 | Thr |
| Ser | Thr | Pro | Leu<br>260 | Ser | Ala | Pro | Val | Ala<br>265 | Pro | Lys | Met | Arg | Leu<br>270 | Gln | Arg |
| Ser | Gln | Ser<br>275 | Asp | Ala | Ala | Arg | Arg<br>280 | Lys | Arg | Leu | Thr | Ser<br>285 | Thr | Gly | Glu |
| Asp | Glu<br>290 | Arg | Glu | Tyr | Gln | Ser<br>295 | Asp | His | Glu | Ala | Thr<br>300 | Trp | Asp | Glu | Phe |
| Gly | Asp<br>305 | Arg | Tyr | Asp | Asn | Phe<br>310 | Thr | Ala | Gly | Arg<br>315 | Glu | Arg | Leu | Gln | Glu<br>320 |
| Phe | Asn | Gly | Arg | Ile<br>325 | Pro | Pro | Arg | Lys | Lys<br>330 | Lys | Ser | Ser | Asn | Ser<br>335 | His |
| Ser | Ser | Ser | Ser<br>340 | Asn | Asn | Pro | Val | Cys<br>345 | His | Thr | Asp | Ser | Gln<br>350 | Ser | Gly |
| Gly | Thr | Ser<br>355 | Gln | Ala | Glu | Ser | Gly<br>360 | Ala | Ile | His | Gly | His<br>365 | Ile | Ser | Gln |
| Gln | Arg<br>370 | Gln | Val | Glu | Arg | Glu<br>375 | Arg | Gln | Lys | Ala | Lys<br>380 | Ala | Glu | Lys | Lys |
| Lys<br>385 | Pro | Gln | Ser | Phe | Thr<br>390 | Trp | Pro | Thr | Val | Val<br>395 | Thr | Val | Phe | Val | Leu<br>400 |
| Ala | Met | Gly | Cys | Gly<br>405 | Phe | Phe | Ala | Ala | Arg<br>410 |  |  |  |  |  |  |

( 2 ) INFORMATION FOR SEQ ID NO:6:

( i ) SEQUENCE CHARACTERISTICS:
        ( A ) LENGTH: 3900 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:6:

TGACAAAAAA TAAAAAACGA AATCCATCGT GAACAGTTTT GTGTTTTTAA ATCAGTTCTA    60

-continued

| | | | | | |
|---|---|---|---|---|---|
| AACACGAAAA | GGGTTGATGA | AAAACGCAGA | AGAATCCGAA | AAACTAACTA | ACCGAGCAAA | 120
| AACTTGACTT | GAGTGTTGTT | TGACAAATCA | GGAAAGATAA | AAAACAAATC | ATAAGAAAAA | 180
| ACTGCACGAA | AAATGAAAAA | GTTTCTAATA | TTCAAAATCT | TGCACAAGAA | ATACAAAATC | 240
| AATTAAAGTG | AACTCTAACC | AAAAGTTGTA | CACAAAATAA | AAAGCAAAAC | AAAGCAGCGA | 300
| AGAACAATCA | CAAGAAGAGC | AAAGTGCCAA | CAAAGTGCAG | GAAGGAAGGA | AGCGGATAAG | 360
| GACAAAAAGG | AAGCCAGCAC | ACACACACAC | ACCCACACAA | TGGCCGTGCC | CTTTTATTTG | 420
| CCCGAGGGCG | CGCCGATGA | CGTAGCGTCG | AGTTCATCGG | GAGCCTCGGG | CAACTCCTCC | 480
| CCCCACAACC | ACCCACTTCC | CTCGAGCGCA | TCCTCGTCCG | TCTCCTCCTC | GGGCGTGTCC | 540
| TCGGCCTCCG | CCTCCTCGGC | CTCATCTTCG | TCATCCGCAT | CGTCGGACGG | CGCCAGCAGC | 600
| GCCGCCTCGC | AATCGCCGAA | CACCACCACC | TCGTCGGCCA | CGCAGACGCC | GATGCAGTCT | 660
| CCACTGCCCA | CCGACCAAGT | GCTATACGCC | CTCTACGAGT | GGGTCAGGAT | GTACCAGAGC | 720
| CAGCAGAGTG | CCCCGCAAAT | CTTCCAGTAT | CCGCCGCCAA | GCCCTCTTG | CAATTTCACT | 780
| GGCGGCGATG | TGTTCTTTCC | GCACGGCCAT | CCGAATCCGA | ACTCGAATCC | CCATCCGCGC | 840
| ACCCCCCGAA | CCAGCGTGAG | CTTCTCCTCC | GGCGAGGAGT | ACAACTTCTT | CCGGCAGCAG | 900
| CAGCCGCAAC | CACATCCGTC | ATATCCGGCG | CCATCAACAC | CGCAGCCAAT | GCCACCGCAG | 960
| TCAGCGCCGC | CGATGCACTG | CAGCCACAGC | TACCCGCAGC | AGTCGGCGCA | CATGATGCCA | 1020
| CACCATTCCG | CTCCCTTCGG | AATGGGCGGT | ACCTACTACG | CCGGCTACAC | GCCACCACCC | 1080
| ACTCCGAACA | CGGCCAGTGC | GGGCACCTCC | AGCTCATCGG | CGGCCTTCGG | CTGGCACGGC | 1140
| CACCCCCACA | GCCCCTTCAC | GTCGACCTCC | ACGCCGTTAT | CGGCGCCAGT | GGCGCCCAAG | 1200
| ATGCGCCTGC | AGCGCAGCCA | GTCGGATGCG | GCCAGACGCA | AGCGATTGAC | CTCGACGGGC | 1260
| GAGGATGAGC | GCGAGTACCA | GAGCGATCAT | GAGGCCACTT | GGGACGAGTT | TGGCGATCGC | 1320
| TACGACAACT | TTACGGCCGG | CCGGGAGCGT | CTGCAGGAGT | TCAATGGACG | CATCCCGCCC | 1380
| CGGAAGAAGA | AGAGCTCCAA | TAGCCACTCG | AGCAGCAGCA | ATAATCCAGT | CTGCCATACC | 1440
| GACAGCCAGT | CCGGTGGTAC | ATCCCAAGCG | GAGAGCGGTG | CCATCCATGG | CCACATCAGT | 1500
| CAGCAGCGAC | AGGTGGAGCG | AGAACGACAA | AAGGCGAAGG | CCGAGAAGAA | GAAACCACAG | 1560
| AGCTTCACTT | GGCCAACTGT | TGTGACCGTT | TTCGTTTTGG | CCATGGGCTG | TGGCTTCTTT | 1620
| GCGGCGCGAT | GAAAGCGCAG | GAGACGTGTA | ATCGAATGAT | CTATAGTGAA | ATCAGCTAGC | 1680
| CCTTAAGATA | TATGCCGATC | TAAACATAGT | TGTAGTTAAA | CCGTACATAA | GTGCAACGAA | 1740
| TTTATTGAAC | TGCAGGAGCG | AAAGCAGAAA | GTCATTAATT | CGTAAACGGA | TTGTTAGATA | 1800
| CACAAACAGC | CAACATACAC | GAAGAGTGTG | CCTAAGATTA | AGAAGGTTGA | CGGGACACAA | 1860
| GAACAATATA | TTCTATCTGT | CTATGGTAAC | TGCATTTGTA | TTTCTAAAAC | GAAACGAAAG | 1920
| ATAACAATCT | TAACTGCTCA | AAGTAATGAA | AACTCTTAGA | CTGGCAAGAG | ACTCAAATCA | 1980
| CACTTATTTT | TTTGCTGATC | CATATTTTTG | TACAACCTTT | TGAGCGATAT | TTACAAATTA | 2040
| TACTAGTACA | AAAAAAAGAG | AGAGAGAGAT | AAGCAAAAGA | AAACTGCCAC | TTTTGAGATA | 2100
| CTTTGATAA | TCTTTGATTT | GCATTAATC | ATTTCCACAC | TTGCATTTTT | TATAAACAAC | 2160
| AAACAAAATT | ACTTCCATTG | TAGAACAAAG | TAAACTGCAA | TTTCAATGTC | TTCGCATTTG | 2220
| TAATTCCGAA | TTGCAAGAAA | AACAAAAATA | TTTTAAATAT | GTTAACTAG | TAGAATTTTT | 2280
| TAAACGTAAG | TCCACAAAAA | CAAGCACATC | TAGCTTTAAT | TGTTGAAACA | AAAGCAGAAA | 2340
| AAACGCAACA | AAAAAATGAA | TGAAAATCAT | TAAATTAATT | TTGTATATAG | TTTTTATGCC | 2400
| ATTTTTGTGA | TGTTTTGTGT | CTACGGTTTA | TGTCATGTTA | TTTTAGTTAA | ATTTCTTATG | 2460

| | | | | | |
|---|---|---|---|---|---|
| ATTTATGTTT | ATTTGTAATA | TTTTTTGTCA | TTGTTTGTTC | ATCATCATAT | TCAAATTGGT 2520 |
| CTCACAATAT | AATAGTTTTA | AGCTCCACGC | CCGGGAGATT | GATGGCAAAA | CGATTGAAAT 2580 |
| TTGGCCAGAA | GAGAGATAGT | TTTCCCCATT | CGTACACAGT | CTTTTTTGGA | ATGCACATTA 2640 |
| ATGATCTCTC | ACAATGGAAA | TTAATGAAAA | TTGATCTCCG | CAGCTAGCCA | AAGTTAAAAA 2700 |
| AGAAATGAAG | AGGAAAACAT | ATTCTATAGG | CAATTTTCAC | TATATGCTAG | AATTTCCCGG 2760 |
| GCGTTTCAAT | GCTAATCGAA | TACAGTGACA | TGAAAGCAAA | CATAGCGAAA | ATATTAAGAA 2820 |
| AATCAATCAA | AAAGAAAGAA | AAACCAATTC | CCAAAAATCG | CATTGATCTC | ATGGATTTAT 2880 |
| ACAATACAAT | TACATCAACC | GTTTTTTTAC | AATGAGAAAT | GTTATAAAAA | GCAGAAAGTG 2940 |
| AAACACAGAA | ACATAAACAA | AAATTAACGA | AAAGCTTAGA | TATAAGTTCG | CCAAGCGTTT 3000 |
| TAGTTCTATT | TTCTAGAATG | TCTAAGTCGG | TTTAGTGAGT | TTATTAAGCT | GTCTTCGGAC 3060 |
| ACAAGTTTAT | TTGTATATAA | GCAATATTAT | TTGTGTAGCC | TAAGTGACAG | TCCCAATCAA 3120 |
| ATCCAATCCA | ATATCACCCA | GTCCCGGACA | TTTCCCAGCA | AAACAATAGA | CTATTCTCGC 3180 |
| GTTCACATGT | ATCAATCTTA | ATTTGAATTA | CCACAAAATG | AAATGAAATA | CTAAAACCAT 3240 |
| ACACAAATGA | AAAATTATTT | TTGTAAATTG | TTTGCATCAA | GTGAGCAAGG | GGATTAGATT 3300 |
| AAGGAATCAT | CCTTGCTTTA | TCCCTGCTT | ATTGCTAATT | AGTTTTCACA | ATGATCTCGG 3360 |
| TAAAGTTTTG | TGGCCTTGCG | CCCAAAAGTC | GTACAGATTT | TTGGTTTGCC | ATAAATACTC 3420 |
| GAACAAAAAG | TTAATGAAAA | ACGAAGCAAA | TGGAAAAAAA | ATCAGAATGA | AACACAAGAA 3480 |
| ATTTATATTT | TTGACCCAAT | GCTACTTAAT | CCGTTTTTGT | AATTTAAGTA | TCTTTACTCG 3540 |
| ACCTTGTATA | TAGCGCAGTT | CGAATCACAG | AATCAAATGC | CATTTTTGTA | TAGAATTTTA 3600 |
| TTTGGTGCCA | AAACAGTGAC | AGATAATTAA | ATGTCTATGA | ACCCGTGTAT | TTCGCATATT 3660 |
| ATACATTTAT | ACATATATCG | TAACTTCAAT | GATAAGTTTG | ATTCTGAAAT | TTTGTCAACT 3720 |
| CAATTTAAGA | AACATTTCTG | TTGTAGTTTA | GTGATTGCTA | GCAGAAAGCA | CTTTGTTTAA 3780 |
| TTGTACATTT | TATATTATGC | TGTAATATTT | TAATATACAT | AAATATCATT | ATTGATCTCA 3840 |
| TGAATATGTT | CATAAGACAA | CAAAAATTAT | ATATATGAAT | ACATCTATGT | GTATGTGTAA 3900 |

( 2 ) INFORMATION FOR SEQ ID NO:7:

( i ) SEQUENCE CHARACTERISTICS:
        ( A ) LENGTH: 410 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

```
    Met Ala Val Pro Phe Tyr Leu Pro Glu Gly Gly Ala Asp Asp Val Ala
    1               5                   10                  15

Ser Ser Ser Ser Gly Ala Ser Gly Asn Ser Ser Pro His Asn His Pro
                    20                  25                  30

Leu Pro Ser Ser Ala Ser Ser Val Ser Ser Gly Val Ser Ser
                35                  40                  45

Ala Ser Ala Ser Ser Ala Ser Ser Ser Ser Ala Ser Ser Asp Gly
            50                  55                  60

Ala Ser Ser Ala Ala Ser Gln Ser Pro Asn Thr Thr Ser Ser Ala
    65                  70                  75                  80

Thr Gln Thr Pro Met Gln Ser Pro Leu Pro Thr Asp Gln Val Leu Tyr
                    85                  90                  95

Ala Leu Tyr Glu Trp Val Arg Met Tyr Gln Ser Gln Gln Ser Ala Pro
```

|     |     |     |     |     |     |     | 100 |     |     |     | 105 |     |     |     | 110 |     |     |
|---|---|---|---|---|---|---|---|---|---|---|---|---|---|---|---|---|---|

Gln Ile Phe Gln Tyr Pro Pro Pro Ser Pro Ser Cys Asn Phe Thr Gly
115                             120             125

Gly Asp Val Phe Phe Pro His Gly His Pro Asn Pro Asn Ser Asn Pro
130                 135                 140

His Pro Arg Thr Pro Arg Thr Ser Val Ser Phe Ser Ser Gly Glu Glu
145             150             155                         160

Tyr Asn Phe Phe Arg Gln Gln Gln Pro Gln Pro His Pro Ser Tyr Pro
165                     170                     175

Ala Pro Ser Thr Pro Gln Pro Met Pro Pro Gln Ser Ala Pro Pro Met
180                     185                 190

His Cys Ser His Ser Tyr Pro Gln Gln Ser Ala His Met Met Pro His
195                     200                 205

His Ser Ala Pro Phe Gly Met Gly Gly Thr Tyr Tyr Ala Gly Tyr Thr
210             215                 220

Pro Pro Pro Thr Pro Asn Thr Ala Ser Ala Gly Thr Ser Ser Ser Ser
225             230                 235                     240

Ala Ala Phe Gly Trp His Gly His Pro His Ser Pro Phe Thr Ser Thr
245                     250                 255

Ser Thr Pro Leu Ser Ala Pro Val Ala Pro Lys Met Arg Leu Gln Arg
260                 265                 270

Ser Gln Ser Asp Ala Ala Arg Arg Lys Arg Leu Thr Ser Thr Gly Glu
275                     280                 285

Asp Glu Arg Glu Tyr Gln Ser Asp His Glu Ala Thr Trp Asp Glu Phe
290                 295                 300

Gly Asp Arg Tyr Asp Asn Phe Thr Ala Gly Arg Glu Arg Leu Gln Glu
305             310                 315                 320

Phe Asn Gly Arg Ile Pro Pro Arg Lys Lys Lys Ser Ser Asn Ser His
325                     330                         335

Ser Ser Ser Ser Asn Asn Pro Val Cys His Thr Asp Ser Gln Ser Gly
340                 345                     350

Gly Thr Ser Gln Ala Glu Ser Gly Ala Ile His Gly His Ile Ser Gln
355                 360                 365

Gln Arg Gln Val Glu Arg Glu Arg Gln Lys Ala Lys Ala Glu Lys Lys
370                 375                 380

Lys Pro Gln Ser Phe Thr Trp Pro Thr Val Val Thr Val Phe Val Leu
385             390                 395                 400

Ala Met Gly Cys Gly Phe Phe Ala Ala Arg
405             410

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

GAGTGGGTCA GGATGTACCA GAGCCAGC                  28

( 2 ) INFORMATION FOR SEQ ID NO:9:

( i ) SEQUENCE CHARACTERISTICS:
        ( A ) LENGTH: 66 base pairs
        ( B ) TYPE: nucleic acid (C) STRANDEDNESS: unknown
(D) TOPOLOGY: unknown (ii) MOLECULE TYPE: DNA (genomic)

(xi) SEQUENCE DESCRIPTION: SEQ ID NO:9:

GAGTGGGTCA GGATGTACCA TGATGAAATA ACATTTTATT TCATCATGGG ATGTACCAGA    60

GCCAGC    66

(2) INFORMATION FOR SEQ ID NO:10:

(i) SEQUENCE CHARACTERISTICS:
    (A) LENGTH: 68 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:10:

GAGTGGGTCA GGATGTACCA TGATGAAATA ACATATGTTA TTTCATCATG GGATGTACCA    60

GAGCCAGC    68

(2) INFORMATION FOR SEQ ID NO:11:

(i) SEQUENCE CHARACTERISTICS:
    (A) LENGTH: 20 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:11:

ATGGCNGTGG CNTTCTAYAT    20

(2) INFORMATION FOR SEQ ID NO:12:

(i) SEQUENCE CHARACTERISTICS:
    (A) LENGTH: 7 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:12:

Met Ala Val Ala Phe Tyr Leu
 1               5

(2) INFORMATION FOR SEQ ID NO:13:

(i) SEQUENCE CHARACTERISTICS:
    (A) LENGTH: 17 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:13:

CCGGTCTTNG GRTGRCA    17

(2) INFORMATION FOR SEQ ID NO:14:

(i) SEQUENCE CHARACTERISTICS:
    (A) LENGTH: 752 base pairs
    (B) TYPE: nucleic acid ( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:14:

| GTTTGATTTT | CTTATTATGT | GCCAACTGTA | TTTAAATTGT | CATTCGCTTA | ACTTTCGTTT | 60 |
| CAGCCCCGCA | AATCTTCCAG | TATCCGCCGC | CAAGCCCCTC | TTGCAATTTC | ACTGGCGGCG | 120 |
| ATGTGTTCTT | TCCGCACGGC | CATCCGAATC | CGAACTCGAA | TCCCCATCCA | CGTACCCCCC | 180 |
| GAACCAGCGT | GAGCTTCTCC | TCCGGCGAGG | AGTACAACTT | CTTCCGGCAG | CAGCAGCCGC | 240 |
| AACCACATCC | GTCATATCCG | GCGCCATCAA | CACCGCAGCC | AATGCCACCG | CAGTCAGCGC | 300 |
| CGCCGATGCA | CTGCAGCCAC | AGCTACCCGC | AGCAGTCGGC | GCACATGATG | CCACACCATT | 360 |
| CCGCTCCCTT | CGGAATGGGC | GGTACCTACT | ACGCCGGCTA | CACGCCGCCA | CCCACTCCGA | 420 |
| ACACGGCCAG | TGCGGGCACC | TCCAGCTCAT | CGGCGGCCTT | CGGCTGGCAC | GGCCACCCCC | 480 |
| ACAGCCCCTT | CACGTCGACC | TCCACGCCGT | TATCGGCGCC | AGTGGCGCCC | AAGATGCGCC | 540 |
| TGCAGCGCAG | CCAGTCGGAT | GCGGCCAGAC | GGTGAGTAGC | CAGCGATGCA | GGGTGCCAAA | 600 |
| AGATACACTG | CCTGGGTGGT | GCAAATCAAA | TCAAACTGTA | ATTTAGATTC | AGATCGATGA | 660 |
| GCATACAGAA | TAAGAGGGAA | AGTTCCGAAC | TATGACATGA | TAGGATGCCA | TTTAGACCAA | 720 |
| GTAAAATATA | CAAAGCTATA | CACAGATTGT | AT | | | 752 |

( 2 ) INFORMATION FOR SEQ ID NO:15:

( i ) SEQUENCE CHARACTERISTICS:
( A ) LENGTH: 503 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:15:

| GCTACACAAA | CCCGAATCGA | ATCCGAACCG | ACTGATAATT | GCTCATGACG | TTCCAAGTCA | 60 |
| ACCGTCTATA | TGTGCAGCGA | TATTTATAGT | CCCNTTATGC | GTCTCTTCCC | ACAGCAAGCG | 120 |
| ATTGACCTCG | ACGGGCGAGG | ATGAGCGCGA | GTACCAGAGC | GATCATGAGG | CCACTTGGGA | 180 |
| CGAGTTTGGC | GATCGCTACG | ACAACTTTAC | GGCCGGCCGG | GAGCGTCTGC | AGGAGTTCAA | 240 |
| TGGACGCATC | CCGCCCCGGA | AGAAGAAGAG | CTCCAATAGC | CACTCGAGCA | GCAGCAATAA | 300 |
| TCCAGTCTGC | CATACCGACA | GCCAGTCCGG | TGGTACATCC | CAAGCGGAGA | GCGGTGCCAT | 360 |
| CCATGGCCAC | ATCAGTCAGC | AGCGACAGGT | GGAGCGAGAA | CGACAAAAGG | CGAAGGCCGA | 420 |
| GAAGAAGGTA | AGAAATGGCC | ACCAATCTTG | GAATGCACAA | CGCATACAGA | GAAAGGGTAT | 480 |
| TCTCGTTTCG | GTTAATCAGT | ATC | | | | 503 |

( 2 ) INFORMATION FOR SEQ ID NO:16:

( i ) SEQUENCE CHARACTERISTICS:
( A ) LENGTH: 292 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:16:

| AAAGCAACTT | GTTCTTTATG | TTTAAGATTT | GCCTTCACGT | GCACCTGAAT | ATAACTAAAT | 60 |
| GCTATTTTTT | CTATTCTCCT | TTCAGAAACC | ACAGAGCTTC | ACTTGGCCAA | CTGTTGTGAC | 120 |

| | | | | | | |
|---|---|---|---|---|---|---|
| CGTTTTCGTT | TTGGCCATGG | GCTGTGGCTT | CTTTGCGGCG | CGATGAAAGC | GCAGGAGACG | 180 |
| TGTAATCGAA | TGATCTATAG | TGAAATCAGC | TAGCCCTTAA | GATACATCCG | ATCTAAACTT | 240 |
| AGTTGTAGTT | AAACCGTACA | TAANTGCAAC | GAATTTATTG | AACTGCAGGA | GC | 292 |